US006884216B2

(12) United States Patent
Abe et al.

(10) Patent No.: US 6,884,216 B2
(45) Date of Patent: Apr. 26, 2005

(54) ULTRASOUND DIAGNOSIS APPARATUS AND ULTRASOUND IMAGE DISPLAY METHOD AND APPARATUS

(75) Inventors: Yasuhiko Abe, Otawara (JP); Takuya Sasaki, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/724,104

(22) Filed: Dec. 1, 2003

(65) Prior Publication Data

US 2004/0111028 A1 Jun. 10, 2004

(51) Int. Cl.[7] .................................................. A61B 8/00
(52) U.S. Cl. ..................................... 600/440; 600/450
(58) Field of Search ............................. 600/440, 441, 600/443, 447, 450, 454–456

(56) References Cited

U.S. PATENT DOCUMENTS

| | | | |
|---|---|---|---|
| 5,568,812 A | * | 10/1996 | Murashita et al. .......... 600/440 |
| 5,701,897 A | | 12/1997 | Sano |
| 5,785,654 A | | 7/1998 | Iinuma et al. |
| 5,820,561 A | | 10/1998 | Olstad et al. |
| 6,537,221 B1 | * | 3/2003 | Criton et al. ............... 600/454 |
| 6,638,221 B1 | | 10/2003 | Abe et al. |

* cited by examiner

Primary Examiner—Francis J. Jaworski
(74) Attorney, Agent, or Firm—Oblon, Spivak, McClelland, Maier & Neustadt, P.C.

(57) ABSTRACT

An ultrasound diagnosis apparatus comprising an ultrasound probe which includes ultrasound transducers, transmission/reception unit, a physiological characteristic image data generating unit which generates physiological characteristic image data, which is used to image at least one physiological characteristic of the object, an LOI setting unit which sets an LOI at an arbitrary position on a physiological characteristic image displayed, an M-mode image generating unit which generates an arbitrary M-mode image based on the physiological characteristic image data corresponding to the LOI, a setting unit which sets a profile position by using a cursor, a profile generating unit which generates a temporal profile of the arbitrary M-mode image at the profile position and a spatial profile of the arbitrary M-mode image which is associated with a line segment including at least the LOI, and a display unit which simultaneously displays the arbitrary M-mode image, the temporal profile, and the spatial profile.

29 Claims, 12 Drawing Sheets

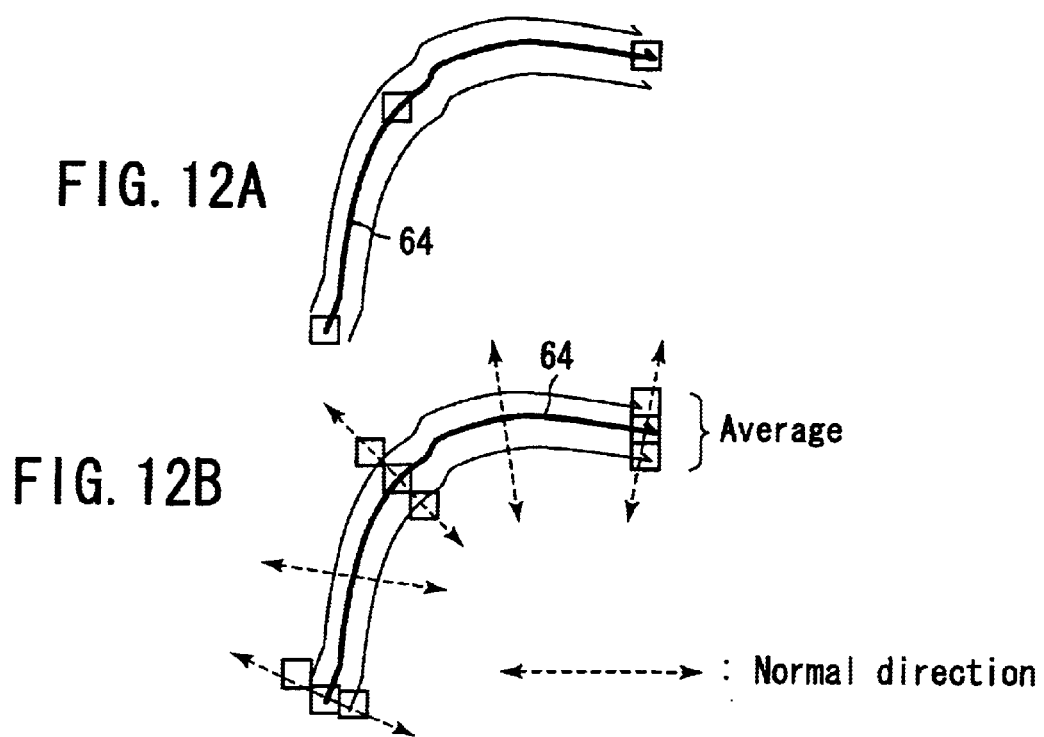
FIG. 12A
FIG. 12B
← - - - → : Normal direction
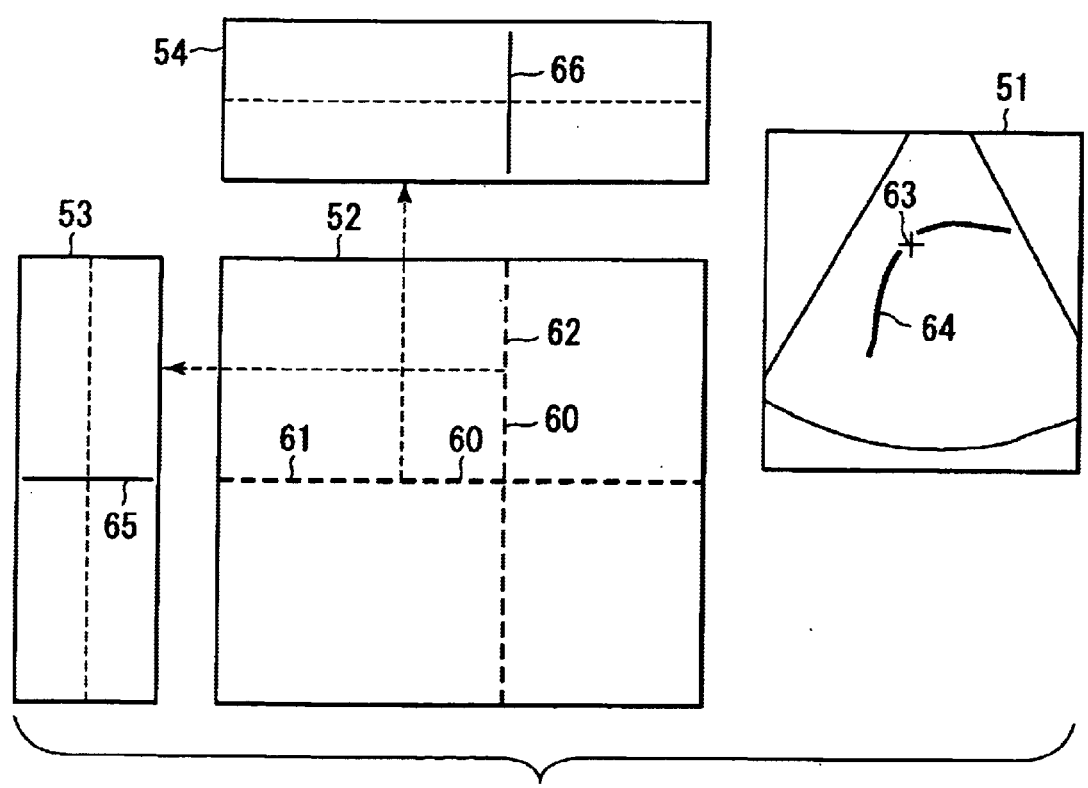
FIG. 13

ULTRASOUND DIAGNOSIS APPARATUS AND ULTRASOUND IMAGE DISPLAY METHOD AND APPARATUS

BACKGROUND OF THE INVENTION

1. Field of the Invention

The present invention relates to an ultrasound diagnosis apparatus and, more particularly, to an ultrasound diagnosis apparatus having a function of analyzing the motion information, blood flow information, and the like of living tissue, an ultrasound image display apparatus, and an ultrasound image display method.

2. Description of the Related Art

An ultrasound diagnosis apparatus emits ultrasound waves generated by ultrasound transducers incorporated in an ultrasound probe into an object to be examined, receives reflected signals originating from acoustic impedance differences in the object tissue through the ultrasound transducers, and displays the resultant image on a monitor.

This diagnosis method allows easy observation of real-time two-dimensional images by simple operation of bringing the ultrasound probe into contact with the body surface, and hence is widely used for functional and morphological diagnoses of organs such as the heart.

In ultrasound diagnosis of tissue such as the heart, in particular, it is very important to objectively and quantitatively evaluate the function of the tissue. The test items in this diagnosis include measurement of the motor function of the heart tissue, the velocity and disturbance of a blood flow, an intracardiac area and volume, and the like.

The M-mode method of repeatedly transmitting and receiving ultrasound waves in a predetermined direction and observing temporal changes in the position of a reflecting region from the resultant reflected signals from the tissue is a test method conventionally used as a technique of quantifying the motion of a cardiac valve or wall or the like.

Conventionally, the M-mode method has been executed on the basis of the locus of luminance on a display window which is determined by the intensity of a reflected signal. Recently, however, with the development of the tissue Doppler method, not only the reflection intensity from an organ such as a cardiac valve or wall but also temporal changes in the movement velocity at the region can be observed. In addition, as disclosed in Jpn. Pat. Appln. KOKAI Publication No. 9-201361, the locus of the movement of an organ can be tracked more accurately from the positional information of a specific region and the movement velocity information of the region which are obtained by the above M-mode method. This has improved the quantification precision of a cardiac function.

In contrast to the conventional M-mode method of displaying temporal changes concerning living tissue in the transmission/reception direction of ultrasound waves, a new M-mode method has been proposed in, for example, Jpn. Pat. Appln. KOKAI Publication Nos. 06-285065 and 10-71147, which extracts biometric information such as a tissue movement velocity in a region along a line segment (LOI (Line of Interest)) set on a two-dimensional image and displays temporal changes in the biometric information by using a display method similar to the conventional M-mode method. In this specification, this new M-mode method (i.e., the M-mode display method associated with an arbitrary LOI which is not limited to the scanning line direction) will be referred to as an "arbitrary M-mode method". According to this method, a wall motion can be easily evaluated by setting a linear LOI on a cardiac wall, blood vessel wall, or the like.

Each of the above references concerning the arbitrary M-mode method, however, described only a method of generating arbitrary M-mode images and a method of displaying such images, but made no mention of a simple, intuitive quantification method concerning arbitrary M-mode image data. That is, in each of the above conventional techniques, an arbitrary M-mode image is observed, and the intensity and the like of the image are determined by measuring with observer's eyes using a color map and the like. This made it impossible to quantitatively evaluate a physiological characteristic of a patient such as a movement velocity in a specific region. Furthermore, since no consideration is given to the correspondence between a time phase or spatial position on an arbitrary M-mode image and a two-dimensional image displayed on the same display window, it is impossible to check the position of a region to be quantified on the two-dimensional image.

BRIEF SUMMARY OF THE INVENTION

The present invention has been made to solve the above problems in the conventional arbitrary M-mode display method, and has as its object to provide an ultrasound diagnosis apparatus, ultrasound image display apparatus, and ultrasound image display method which can easily quantify the motion information of living tissue and hemodynamics information in an arbitrary region in a living body and can be effectively used for clinical diagnosis.

BRIEF DESCRIPTION OF THE SEVERAL VIEWS OF THE DRAWING

FIGS. 12A and 12B are views showing a method of stabilizing M-mode data in the first and second embodiments of the present invention;

FIG. 13 is a view showing another display method in the first and second embodiments of the present invention;

DETAILED DESCRIPTION OF THE INVENTION (First Embodiment)

Physiological characteristics of a patient displayed as arbitrary M-mode images include, for example, the tissue movement velocity of the cardiac muscle or the like obtained by the tissue Doppler method, the displacement or strain of the tissue obtained from the velocity information (see Jpn. Pat. Appln. KOKAI Publication No. 2003-175041), and a strain factor or acceleration. In addition, the blood flow velocity obtained by the color Doppler method or the pressure range or pressure information estimated by applying the Euler's formula to the information obtained from an M-mode image in the heart chamber can be displayed.

Figure 1:
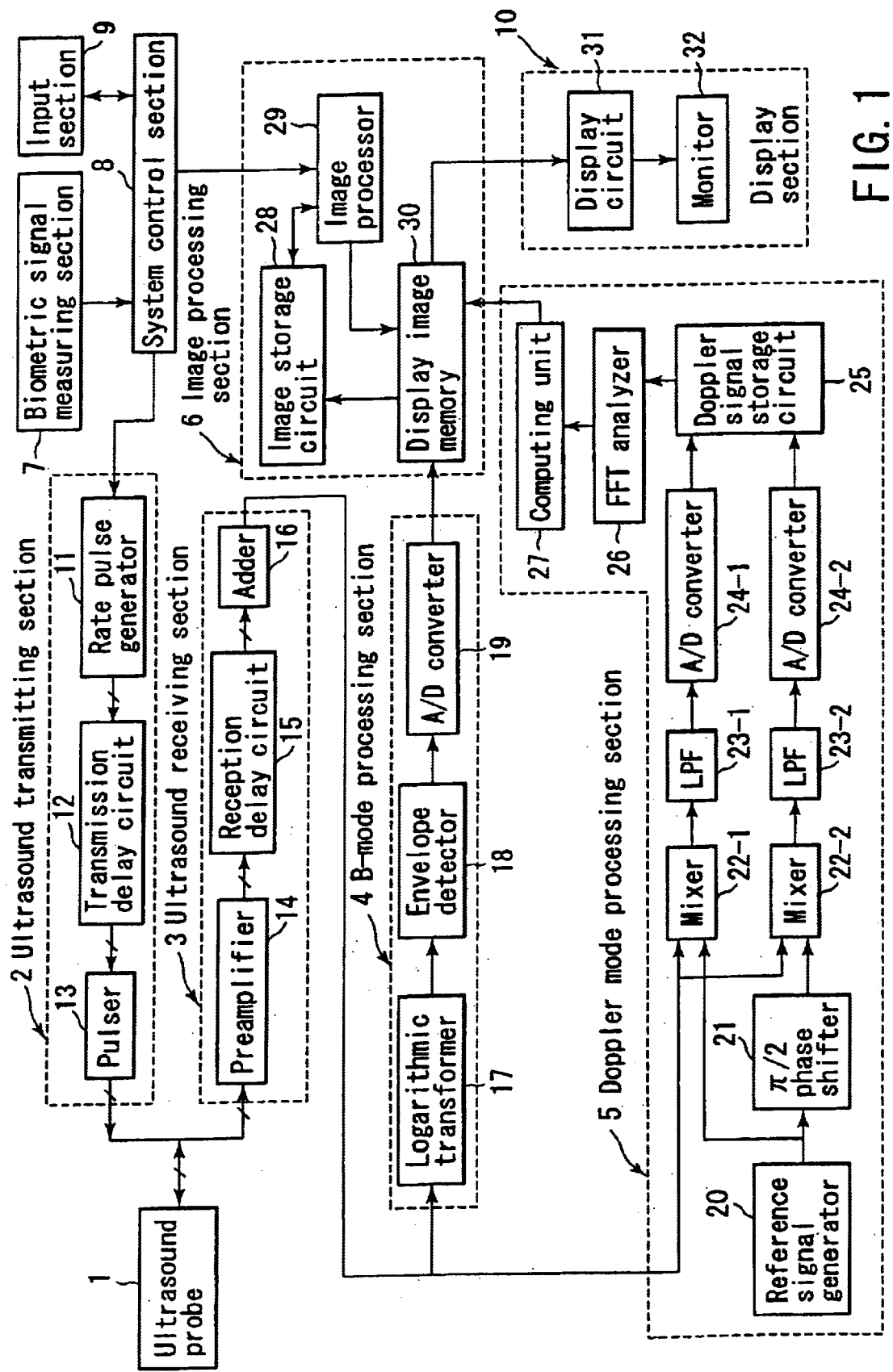
FIG. 1 is a block diagram showing the overall arrangement of an ultrasound diagnosis apparatus according to the first embodiment of the present invention.

An ultrasound diagnosis apparatus and ultrasound image display apparatus according to the first embodiment of the present invention will be described below with reference to FIGS. 1 to 6B, in which the present invention is applied to the two-dimensional image obtained by the B-mode method aimed at the heart and the tissue Doppler method (i.e., the image obtained by combining a B-mode image with a tissue Doppler image). FIG. 1 is a block diagram showing the overall arrangement of the ultrasound diagnosis apparatus according to this embodiment.

This ultrasound diagnosis apparatus and ultrasound image display apparatus include an ultrasound probe 1 which is brought into contact with the surface of an object to be examined to transmit/receive ultrasound waves, an ultrasound transmitting section 2 which generates driving signals for generating ultrasound waves, an ultrasound receiving section 3 which receives ultrasound reflected signals from the interior of the object, a B-mode processing section 4 which performs signal processing for B-mode images with respect to the reception signals, and a Doppler mode processing section 5 which performs signal processing for color Doppler images or tissue Doppler images.

The ultrasound diagnosis apparatus and ultrasound image display apparatus further include an image processing section 6 which displays an arbitrary M-mode image based on a B-mode image or Doppler mode image, together with the spatial profile and temporal profile of velocity information in a designated region on the arbitrary M-mode image, a system control section 8 which systematically controls the respective units, a display section 10, and an input section 9.

The ultrasound probe 1 has its front surface brought into contact with the surface of the object to transmit/receive ultrasound waves. The ultrasound probe 1 has a one-dimensional array of micro-ultrasound transducers mounted on its distal end portion. This ultrasound transducer is an electroacoustic conversion element having a function of converting an electrical pulse into an ultrasound pulse at the time of transmission and converting an ultrasound signal into an electrical signal at the time of reception. An ultrasound frequency that greatly influences the resolution of an ultrasound image or sensitivity is almost determined by the thickness of this ultrasound transducer. The ultrasound probe 1 is small in size and weight and connected to the ultrasound transmitting section 2 and ultrasound receiving section 3 (to be described later) through a cable. As the ultrasound probe 1, one of sector-scan-compatible, linear-scan-compatible, and convex-scan-compatible probes is selected in accordance with a diagnosis region. In the following description, assume that the ultrasound probe 1 designed for the sector scan mode is used.

The ultrasound transmitting section 2 includes a rate pulse generator 11, transmission delay circuit 12, and pulser 13. The rate pulse generator 11 emits rate pulses that determine the repetition period of ultrasound pulses to be emitted into the object. The transmission delay circuit 12 is a delay circuit for determining the convergence distance or deflection angle of an ultrasound beam at the time of transmission. The transmission delay circuit 12 determines the timing when a plurality of ultrasound transducers are driven. The pulser 13 is a driving circuit which generate high-voltage pulses for driving the ultrasound transducers.

The rate pulse generator 11 supplies, to the transmission delay circuit 12, rate pulses that determine the repetition period of ultrasound pulses to be emitted into the body. The transmission delay circuit 12 is constituted by independent delay circuits equal in number to the ultrasound transducers used for transmission. The transmission delay circuit 12 gives rate pulses delay times that make ultrasound waves converge at a predetermined depth to obtain a small beam width in transmission and delay times for the transmission of the ultrasound waves in a predetermined direction, and supplies the rate pulses to the pulser 13.

The pulser 13 has independent driving circuits equal in number to the ultrasound transducers used for transmission. The pulser 13 generates driving pulses for driving the ultrasound transducers incorporated in the ultrasound probe 1 to emit ultrasound waves.

The ultrasound receiving section 3 includes a preamplifier 14, reception delay circuit 15, and adder 16. The preamplifier 14 amplifies small signals converted into electrical signals by the ultrasound transducers and ensures sufficient S/N ratios. The reception delay circuit 15 gives outputs from the preamplifier 14 convergence delay times that make ultrasound waves converge at a predetermined depth to obtain a small reception beam width and delay times that sequentially deflect ultrasound beams in predetermined directions to scan the interior of the object, and supplies the resultant signals to the adder 16. The adder 16 adds a plurality reception signals from the ultrasound transducers to combine them into one signal.

The B-mode processing section 4 includes a logarithmic transformer 17, envelope detector 18, and A/D converter 19. An input signal to the B-mode processing section 4 serves to logarithmically transform the amplitude of a reception signal in the logarithmic transformer 17 so as to relatively enhance a weak signal. In general, a reception signal from the interior of the object has an amplitude with a wide dynamic range of 80 dB or more. In order to display such a reception signal on a general TV monitor with a dynamic range of about 20 to 30 dB, amplitude compression is required to enhance a weak signal. The envelope detector 18 performs envelope detection of the logarithmically transformed reception signal to remove ultrasound frequency components, thereby detecting only the amplitude of the signal. The A/D converter 19 A/D-converts the output signal from the envelope detector 18 to form a B-mode signal.

The Doppler mode processing section 5 includes a reference signal generator 20, $\pi/2$ phase shifter 21, mixer 22, LPF (Low-Pass Filter) 23, A/D converter 24, Doppler signal storage circuit 25, FFT analyzer 26, and computing unit 27.

The Doppler mode processing section 5 mainly performs quadrature phase detection and FFT analysis.

More specifically, an input signal to the Doppler mode processing section 5 is input to the first input terminals of mixers 22-1 and 22-2. An output from the reference signal generator 20, which has almost the same frequency as that of this input signal, is directly sent to the second input terminal of the mixer 22-1. In addition, the output whose phase is shifted by 90° through the $\pi/2$ phase shifter 21 is sent to the second input terminal of the mixer 22-2. Outputs from the mixers 22-1 and 22-2 are sent to low-pass filters 23-1 and 23-2, each of which in turn removes the sum component of an input signal to the Doppler mode processing section 5 and the signal frequency from the reference signal generator 20 to extract only a difference component.

The A/D converter 24 converts outputs from the LPFs 23-1 and 23-2, i.e., quadrature phase detection outputs, into digital signals. The FFT analyzer 26 temporarily stores the digitized quadrature components in the Doppler signal storage circuit 25 and then performs an FFT analysis. The computing unit 27 calculates the center and broadening of the spectrum obtained by the FFT analyzer 26.

The image processing section 6 includes an image storage circuit 28, image processor 29, and display image memory 30.

The image storage circuit 28 stores a two-dimensional image made up of a plurality of B-mode image data and Doppler mode image data obtained at predetermined intervals.

The image processor 29 selects predetermined two-dimensional image data from the image data stored in the image storage circuit 28, and sets an LOI (Line Of Interest) on this image. In this case, an LOI means a line (e.g., a straight line segment, curve, or closed curve) set at an arbitrary position on an ultrasound image as an arbitrary M-mode display target. The image processor 29 also sequentially extracts velocity data at this LOI from a plurality of two-dimensional image data in the image storage circuit 28, and stores the extracted data as arbitrary M-mode image data in the display image memory 30. Furthermore, the image processor 29 obtains the spatial and temporal profiles of velocity information in a predetermined region of this arbitrary M-mode image data and stores them in the display image memory 30.

The display image memory 30 temporarily stores images and characters or numerals such as measurement values to be displayed on the display section 10. At the same time, the display image memory 30 stores cursor data based on an instruction from the input section 9. Note that a B-mode image or Doppler mode image obtained in real time is temporarily stored in the display image memory 30 through the image storage circuit 28.

The system control section 8 controls each of units such as the ultrasound transmitting section 2, ultrasound receiving section 3, B-mode processing section 4, Doppler mode processing section 5, and image processing section 6 and also controls the overall system. The system control section 8 controls the image processing section 6 to send a command from the input section 9 to the image processor 29.

The input section 9 has a keyboard, trackball, mouse, and the like on the operation panel, and is used by the operator of the apparatus to input patient information and imaging conditions for the apparatus. The input section 9 is used, in particular, to set a display command for an arbitrary M-mode image or an LOI or designate the positions of temporal and spatial profiles.

The display section 10 includes a display circuit 31 and monitor 32. The B-mode image or Doppler mode image stored in the display image memory 30 by the image processor 29 is D/A-converted and converted into a TV format, together with an arbitrary M-mode and accompanying time and spatial profiles and the like, in the display circuit 31 to be displayed on the monitor 32.

The biometric signal measuring section 7 has a sensor function of detecting an ECG signal by mounting the measuring section on the body surface of the object, and a function of converting this sensor signal into a digital signal. The ECG signal obtained simultaneously with the time-series two-dimensional images obtained by the biometric signal measuring section 7 is stored in the image storage circuit 28 in association with these two-dimensional image data, and displayed on the display section 10 in correspondence with a temporal profile in arbitrary M-mode display operation.

Figure 2:
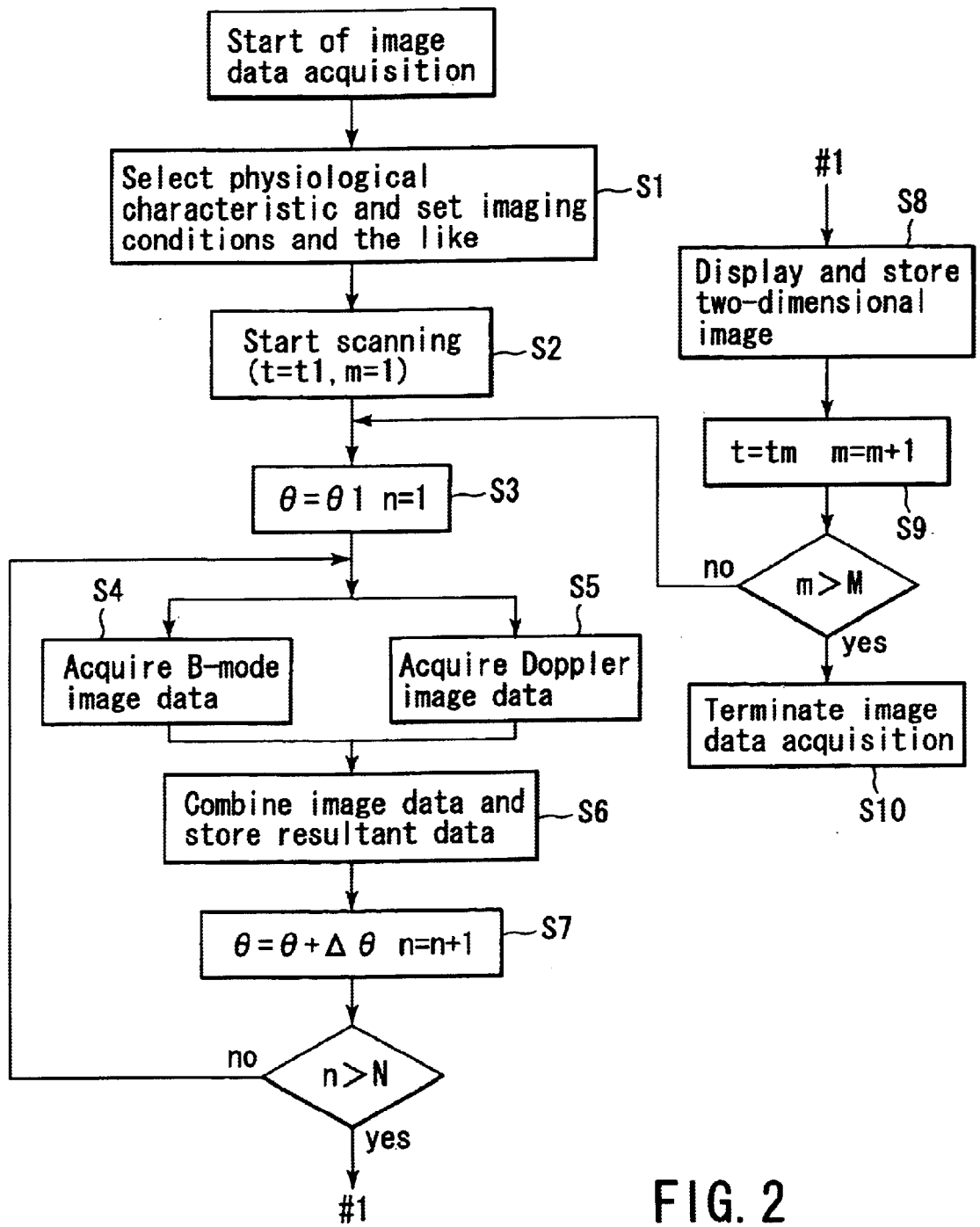
FIG. 2 is a flow chart showing a sequence for acquiring two-dimensional image data in the first embodiment of the present invention.

A sequence for acquiring two-dimensional image data in the first embodiment of the present invention will be described next with reference to FIGS. 1 and 2. FIG. 2 is a flow chart showing a sequence for acquiring two-dimensional image data.

Before the acquisition of image data, the operator operates the input section 9 to set a physiological characteristic of the patient in an arbitrary M-mode image and an interval during which two-dimensional images are acquired (i.e., the time phase of an arbitrary M-mode image), together with imaging conditions for the apparatus. These set values are sent to a memory (not shown) in the system control section 8 to be stored (step S1). In this embodiment, as a physiological characteristic of the patient, the movement velocity of the tissue which can be acquired by the Doppler mode is set, as described above. The time phase is made to correspond to M two-dimensional images during t=t1 to tM. When these settings are complete, the apparatus automatically switches to the imaging mode for two-dimensional images.

The operator fixes the distal end (ultrasound transmission/reception surface) of the ultrasound probe 1 at an optimal position on the body surface of the object and starts scan operation for the acquisition of two-dimensional image data in a time phase t1 (step S2). In practice, the operator determines the above optimal position while observing two-dimensional image data in advance by the same sequence as that described below. In transmitting ultrasound waves, the rate pulse generator 11 supplies, to the transmission delay circuit 12, rate pulses that determine the repetition period of ultrasound pulses to be emitted into the object in synchronism with a control signal from the system control section 8.

The transmission delay circuit 12 is constituted by independent delay circuits almost equal in number to the ultrasound transducers used for transmission. The transmission delay circuit 12 gives rate pulses delay times that make ultrasound waves converge at a predetermined depth to obtain a small beam width in transmission and delay times for the transmission of the ultrasound waves in a predetermined direction ($\theta 1$), and supplies the rate pulses to the pulser 13 (step S3).

Like the transmission delay circuit 12, the pulser 13 has driving circuits almost equal in number to the ultrasound transducers used for transmission. The pulser 13 drives the ultrasound transducers incorporated in the ultrasound probe 1 using the ultrasound transducer driving pulses generated when driven by rate pulses, thereby emitting ultrasound pulses into the body.

Some ultrasound waves emitted into the body are reflected by the interface between organs in the body which have different acoustic impedances or tissue. When such an ultrasound wave is reflected by a moving reflector such as a cardiac wall or blood cell, the ultrasound frequency is subjected to a Doppler shift.

The ultrasound waves reflected by the object tissue are received by the same ultrasound transducers that have transmitted the ultrasound waves, and are converted into electrical signals. The reception signals are amplified by the independent preamplifiers 14 which are almost equal to the ultrasound transducers used for reception. The amplified signals are sent to the reception delay circuits 15 equal in number to the ultrasound transducers used for reception.

The reception delay circuits 15 give the reception signals delay times that make ultrasound waves converge at a predetermined depth to obtain a small beam width in reception and delay times for the reception of an ultrasound beam upon making it have strong reception directivity in a predetermined direction ($\theta 1$), and sends the resultant signals to the adder 16. The adder 16 adds/combines a plurality of reception signals input through the preamplifiers 14 and reception delay circuits 15 to combine them into one reception signal, and sends it to the B-mode processing section 4 and Doppler mode processing section 5.

When B-mode images are to be acquired, an output from the adder 16 is sent to the B-mode processing section 4 to be subjected to logarithmic transformation, envelope detection, and A/D conversion. The resultant data is stored as B-mode image data in the display image memory 30 through the image storage circuit 28 (step S4).

In order to obtain the Doppler shift of an ultrasound reception signal in the Doppler mode processing section 5, the system control section 8 continuously transmits/receives ultrasound waves a plurality of number of times in the same direction ($\theta 1$), and performs FFT (Fast-Fourier-Transform) analysis on the reception signals obtained at this time.

The Doppler mode processing section 5 converts the output from the adder 16 into a complex signal by quadrature phase detection using the mixer 22 and LPF (Low-Pass Filter) 23, and then converts the signal into a digital signal by using the A/D converter 24. The resultant signal is stored in the Doppler signal storage circuit 25. The FFT analyzer 26 obtains the frequency spectrum of a plurality of reception signal data obtained by the same processing as described above for the reception signals obtained by scanning performed a plurality of number of times in the same transmission/reception direction ($\theta 1$) and stored in the Doppler signal storage circuit 25.

The computing unit 27 also calculates the center (the average velocity of a tissue or blood flow) of the frequency spectrum output from the FFT analyzer 26. The system control section 8 stores the calculation result as Doppler mode image data in the display image memory 30, together with the B-mode image data (step S5). At this time, the B-mode image data and Doppler mode image data are combined and stored in the display image memory 30 (step S6).

The frequency spectrum of the Doppler signal obtained by the FFT analyzer 26 includes the tissue Doppler component generated by the motion of a tissue such as the cardiac muscle and the blood flow Doppler component generated by the flow of blood. The former is formed from a component lower in frequency than the latter. When, therefore, a physiological characteristic of the patient in an arbitrary M-mode image is a tissue velocity as in this embodiment, the center of a tissue Doppler component is obtained after a blood flow Doppler component is removed by a means such as filtering.

Note that in calculating the Doppler component of each ultrasound reception signal, the center (i.e., the average velocity), power, or variance value of a Doppler component spectrum may be obtained by using an MTI filter and autocorrelation function instead of using the above method using FFT analysis.

The interior of the object is then scanned in real time by transmitting/receiving ultrasound waves by the same sequence as that described above while sequentially changing the transmission/reception direction of ultrasound sounds $\Delta\theta$ at a time up to $\theta 1+(N-1)\Delta\theta$. At this time, the system control section 8 acquires B-mode image data and Doppler mode image data while sequentially changing the delay times in the transmission delay circuit 12 and reception delay circuit 15 in accordance with the above ultrasound wave transmission/reception direction by using a control signal (steps S4 to S7).

The system control section 8 combines the B-mode image data and Doppler mode image data obtained in steps S4 and S5, respectively, and sequentially stores the resultant data as two-dimensional image data in the display image memory 30. The system control section 8 then displays one-frame two-dimensional image data generated at the time of completion of scanning in the $\theta 1+(N-1)\Delta\theta$ direction on the monitor 32 through the display circuit 31. This two-dimensional image data is stored in the image storage circuit 28 (step 38).

Subsequently, in each of time phases t=t2 to tM, two-dimensional images constituted by B-mode images and Doppler mode images are acquired by the same sequence as that described above (steps S3 to S9). These images are displayed on the monitor 32 in real time through the display image memory 30 and display circuit 31. These image data are sequentially stored in the image storage circuit 28. When M two-dimensional image data are completely stored, the acquisition of two-dimensional image data is terminated (step S10).

Figure 3:
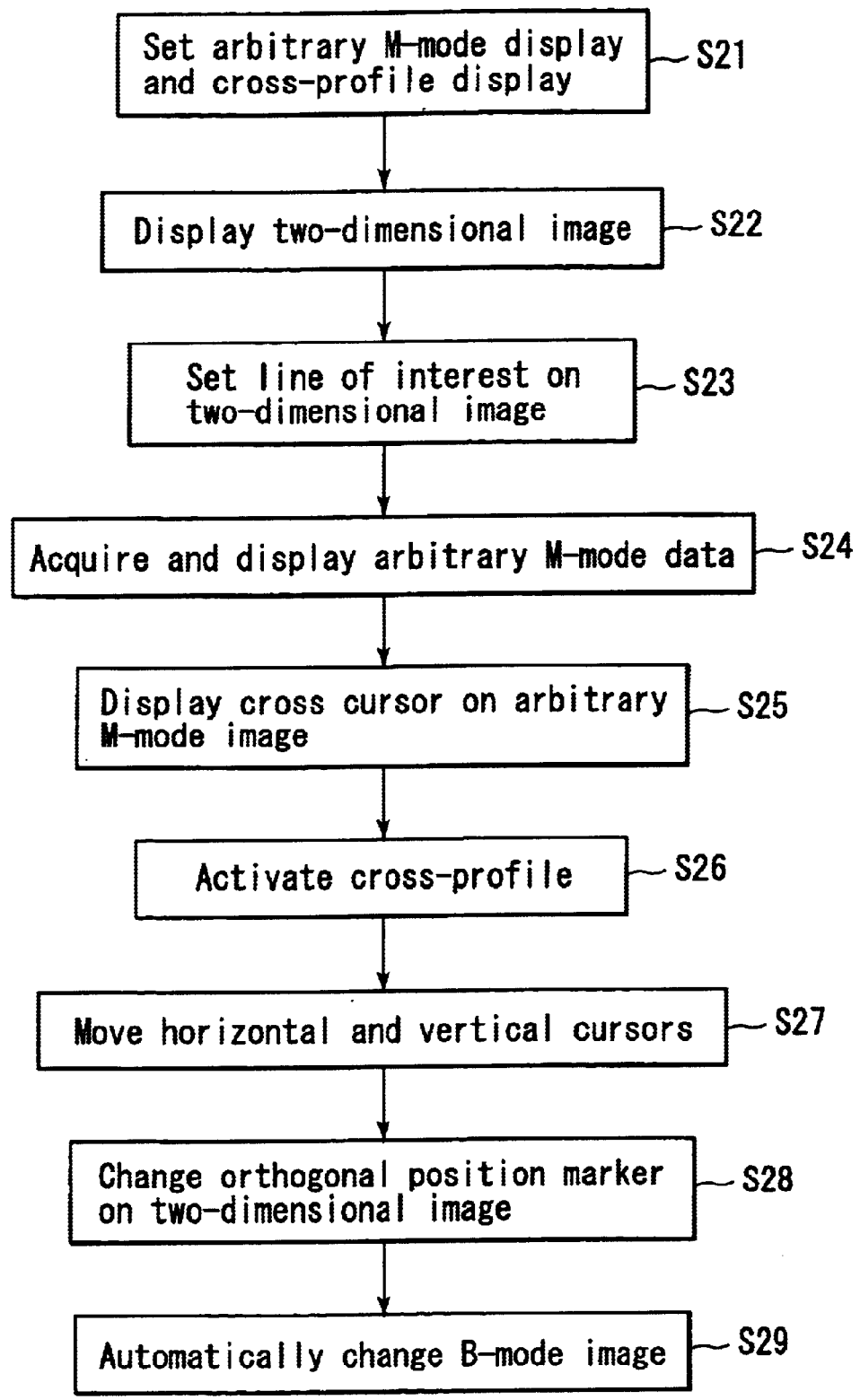
FIG. 3 is a flow chart showing a sequence for displaying a spatial profile and temporal profile in the first embodiment of the present invention.

A sequence for displaying an arbitrary M-mode image and the spatial and temporal profiles of velocity information in a predetermined region on the arbitrary M-mode image by using M two-dimensional images corresponding to one heartbeat which are stored in the image storage circuit 28 in step S8 will be described next with reference to FIGS. 1 and 3 (FIG. 3 is a flow chart showing the display sequence). Note that the temporal profile is a profile of the arbitrary M-mode image along the time axis, and the spatial profile is a profile of the arbitrary M-mode image along the spatial axis.

When the operator presses selection buttons for arbitrary M-mode display and cross-profile display on the console, the corresponding command signals are sent to the image processor 29 through the system control section 8. The image processor 29 displays a display window like the one shown in FIG. 4 on the display section 10 (step S21).

Figure 4:
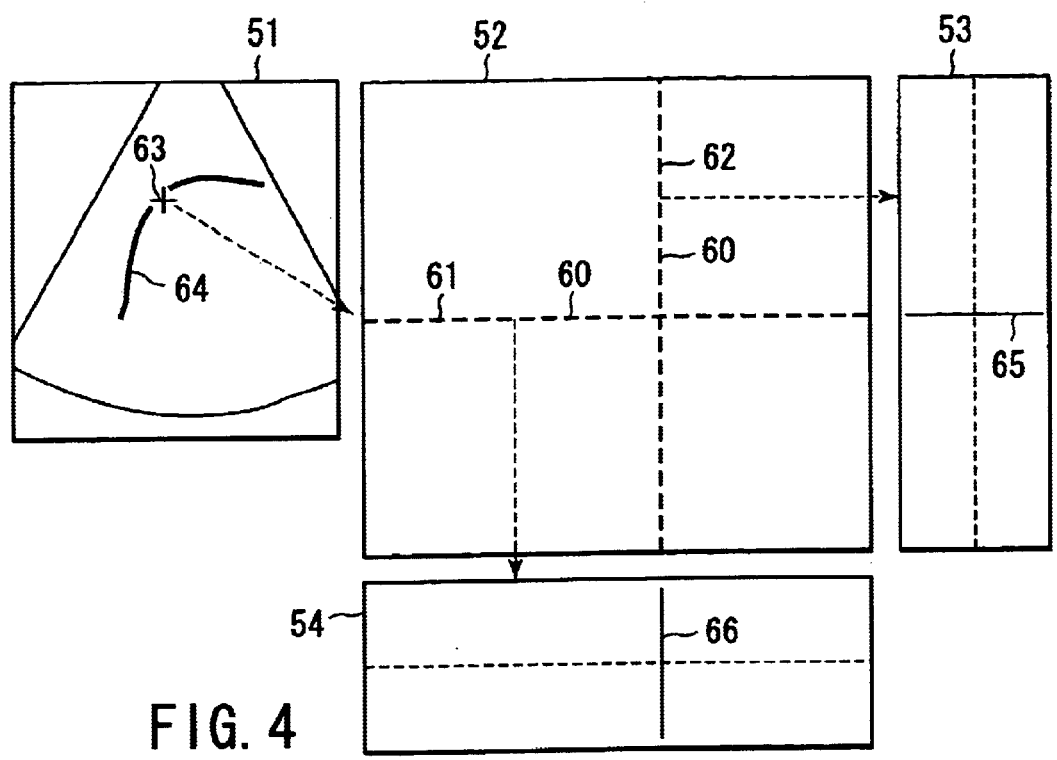
FIG. 4 is a view showing a display method in the first embodiment of the present invention.

FIG. 4 shows a method of displaying an arbitrary M-mode image and physiological characteristics of the patient obtained from this image in this embodiment. As shown in FIG. 4, a first image display area 51 where the two-dimensional image obtained by combining a tissue Doppler image and B-mode image is displayed is set on the left end of the display window on the monitor 32. A second image display area 52 is set in the middle portion of the display window. In the second image display area 52, temporal changes in velocity information of the tissue (i.e., an arbitrary M-mode image) at the linear or curved LOI set by the operator on the two-dimensional image in the first image display area 51 are displayed in luminance (lightness) or color.

The second image display area 52 has a horizontal bar 61 corresponding to each position on the curve set on the arbitrary M-mode image in the time axis direction, and a time bar 62 which intersects the horizontal bar 61 at a right angle and indicates the time phase of the arbitrary M-mode image. A first profile display area 53 in which a spatial profile corresponding to the time bar 62 on the arbitrary M-mode image is displayed is set on the right side of the second image display area 52. A second profile display area 54 in which a temporal profile corresponding to the position of the horizontal bar 61 on the arbitrary M-mode image is set on the lower end of the second image display area 52. In this specification, profile analysis by such arbitrary M-mode display is called cross-profile.

In this cross-profile, profile display of the physiological characteristic of the patient displayed on a generated arbitrary M-mode image is performed. As has been described above, if a plurality of physiological characteristics of the patient can be acquired in the ultrasound diagnosis apparatus, the operator selects the types of physiological characteristics of the patient before the acquisition of M images for the arbitrary M-mode. In this embodiment, the two-dimensional image displayed in the first image display area 51 includes two physiological characteristics of the patient, i.e., the intensity (luminance) of a B-mode image and a tissue Doppler image.

Before starting display in the arbitrary M-mode, the operator makes final selection of a physiological characteristic of the patient to be subjected to quantitative evaluation in cross-profile. The image processor 29 then generates an arbitrary M-mode image in accordance with the selection command, and displays temporal and spatial profiles concerning the physiological characteristic of the patient in cross-profile.

Note that in cross-profile, physiological characteristics of the patient other than B-mode information, such as the above tissue velocity information, is often subjected to quantification. It is therefore preferable that the mode of displaying such physiological characteristics of the patient in the luminance or color of an arbitrary M-mode image be initially set. In cardiac muscle analysis with the injection of a contrast medium, however, the intensity of a B-mode image is preferably selected as a quantification target.

First of all, the operator selects proper two-dimensional image data from the image data stored in the image storage circuit 28, and displays it in the first image display area 51. In general, however, when the operator inputs an arbitrary M-mode command signal to the image processor 29 with the input section 9, two-dimensional image data acquired first (i.e., image data in the time phase t1) is automatically displayed in the first image display area 51 (step S22).

The operator moves the marker displayed on the two-dimensional image displayed in the first image display area 51 in FIG. 4 by using the mouse of the input section 9 to set a linear LOI at an arbitrary position on the two-dimensional image. The image processor 29 measures the total length of this LOI and divides the total length into predetermined intervals or by a predetermined number, thereby determining a position where arbitrary M-mode information (tissue movement velocity) (step S23).

Figure 5:
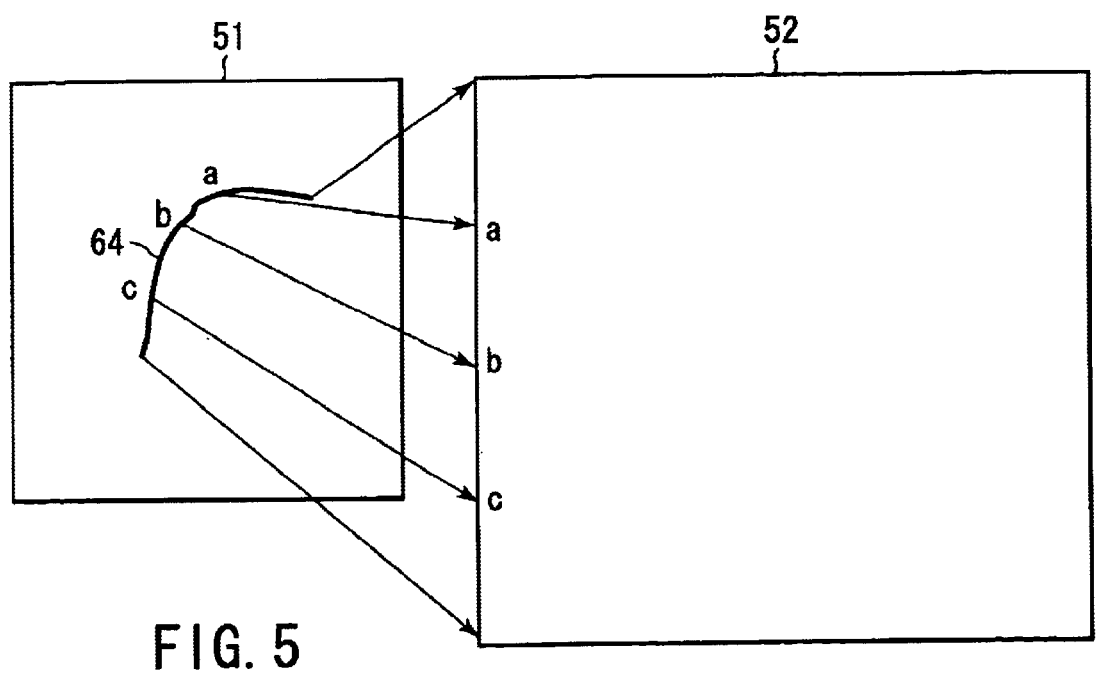
FIG. 5 is a view showing the relationship between an LOI and the ordinate of an arbitrary M-mode image in the first embodiment of the present invention.

FIG. 5 shows the relationship between an LOI 64 set on a two-dimensional image in the first image display area 51 and the ordinate of an arbitrary M-mode image displayed in the second image display area 52. The ordinate is made to correspond to the total length of the LOI 64, and the respective positions (e.g., points a, b, and c) on the LOI 64 are assigned to the ordinate of the arbitrary M-mode image at the same ratios.

When the LOI 64 is set by the operator, the image processor 29 reads the coordinates of each point on the LOI 64. The image processor 29 then reads out the movement velocities of the tissue at the respective positions from the M tissue Doppler image data stored in the image storage circuit 28, and sequentially displays them in the second image display area 52 in time series. Assume that, in the image data acquisition in step SB, M two-dimensional image data corresponding to one heartbeat are to be acquired and stored in the image storage circuit 28. In this case, the image processor 29 reads out velocity information at a predetermined position on the LOI 64 which has already been set in each two-dimensional image data, and sequentially displays the information in the time axis direction of the second image display area 52 in the order of image data acquisition, thereby generating an arbitrary M-mode image corresponding to one heartbeat (step S24).

When the operator clicks an arbitrary position on the arbitrary M-mode image displayed in the second image display area 52 by using the mouse, a cross cursor (cross line) 60 is displayed at the clicked position (step S25). At the same time, cross-profile is activated (step S26). The operator can set the central position of the cross cursor 60, the horizontal bar 61 (which is the horizontal line of the cross cursor 60 and corresponds to a given spatial position in the arbitrary M-mode display), and the time bar 62 (which is the vertical line of the cross cursor 60 and corresponds to a given time in the M-mode display). The operator clicks the central position of the cross cursor 60 by using the mouse, and drags it in an arbitrary direction to move the central position and the position of the cross cursor 60 to desired positions. The operator moves the horizontal bar 61 and time bar 62 to desired positions by independently dragging the respective bars in the vertical and horizontal direction (step S27).

In this manner, the image processor 29 displays, in the first profile display area 53, the spatial profile of a physiological characteristic of the patient at the time (time phase) determined by the position of the time bar 62 on the arbitrary M-mode image. In this case, the display width of the spatial profile in the longitudinal direction is made to coincide with the display width of an arbitrary M-mode image in the longitudinal direction, and the space marker 65 indicating the position of the horizontal bar 61, the positional information of the space marker 65 (e.g., the distance [mm] from the upper end or the ratio [%] of this distance to the length of the LOI), and the numerical information ([mm/sec] or the like) of the physiological characteristic of the patient are also displayed in the spatial profile. The abscissa of the spatial profile indicates the magnitude of the physiological characteristic of the patient (i.e., the velocity of the tissue), and the physiological characteristic of the patient is displayed within a display area with a predetermined size by standardizing the magnitude of the physiological characteristic of the patient.

Likewise, the temporal profile of the physiological characteristic of the patient at a position corresponding to the horizontal bar 61 is displayed in the second profile display area 54. The display width of this profile in the lateral direction is made to coincide with the display width of arbitrary M-mode display in the lateral direction, and a time marker 66 indicating the position of the time bar 62, the time information of the time marker 66 (e.g., a relative time [sec] with reference to the left end of the temporal profile), and the numerical information ([mm/sec] or the like) of the physiological characteristic of the patient are also displayed in the temporal profile. In this case as well, the ordinate of the temporal profile indicates the magnitude of the physiological characteristic of the patient, and the image processor 29 displays this physiological characteristic by standardizing its magnitude.

The operator moves the horizontal bar 61 of the second image display area 52 in the vertical direction by using the mouse of the input section 9. The image processor 29 reads the longitudinal coordinates of the horizontal bar 61 and moves an orthogonal position marker 63 to that position on the LOI 64 on the two-dimensional image which corresponds to the longitudinal coordinates. That is, the orthogonal position marker 63 moves on the LOI 64 in synchronism with the movement of the horizontal bar 61, and the position of the marker is automatically updated. Associating the respective images with each other in real time in this manner allows the operator to easily know the position of an observation point, on the two-dimensional image, on the temporal profile displayed in the second profile display area 54 (step S28).

By moving the orthogonal position marker 63 displayed on the two-dimensional image using the mouse by the same procedure as described above, the operator can update the position of the horizontal bar 61 displayed on the arbitrary M-mode image in the second image display area 52 and the temporal profile displayed in the second profile display area 54.

The time bar 62 corresponds to the time phase of a plurality of (M) two-dimensional images sequentially stored in the image storage circuit 28. Assume that a two-dimensional image in the first image display area 51 is a still image. In this case, when the position of the time bar 62 is associated with the time phase of the two-dimensional image, the two-dimensional image corresponding to the physiological characteristic displayed on the spatial profile is automatically selected to allow observation of the image.

When a two-dimensional image in the first image display area 51 is to be played back as a moving image, a physiological characteristic at the position of the LOI 64 set on the moving image is displayed as an arbitrary M-mode image with M time phases in the second image display area 52. In addition, the time bar 62 on this arbitrary M-mode image moves in accordance with the time phase of the two-dimensional image. Meanwhile, spatial profiles at the portions whether the time bar 62 moves are sequentially displayed in the first profile display area 53 (step S29).

Figure 6A:
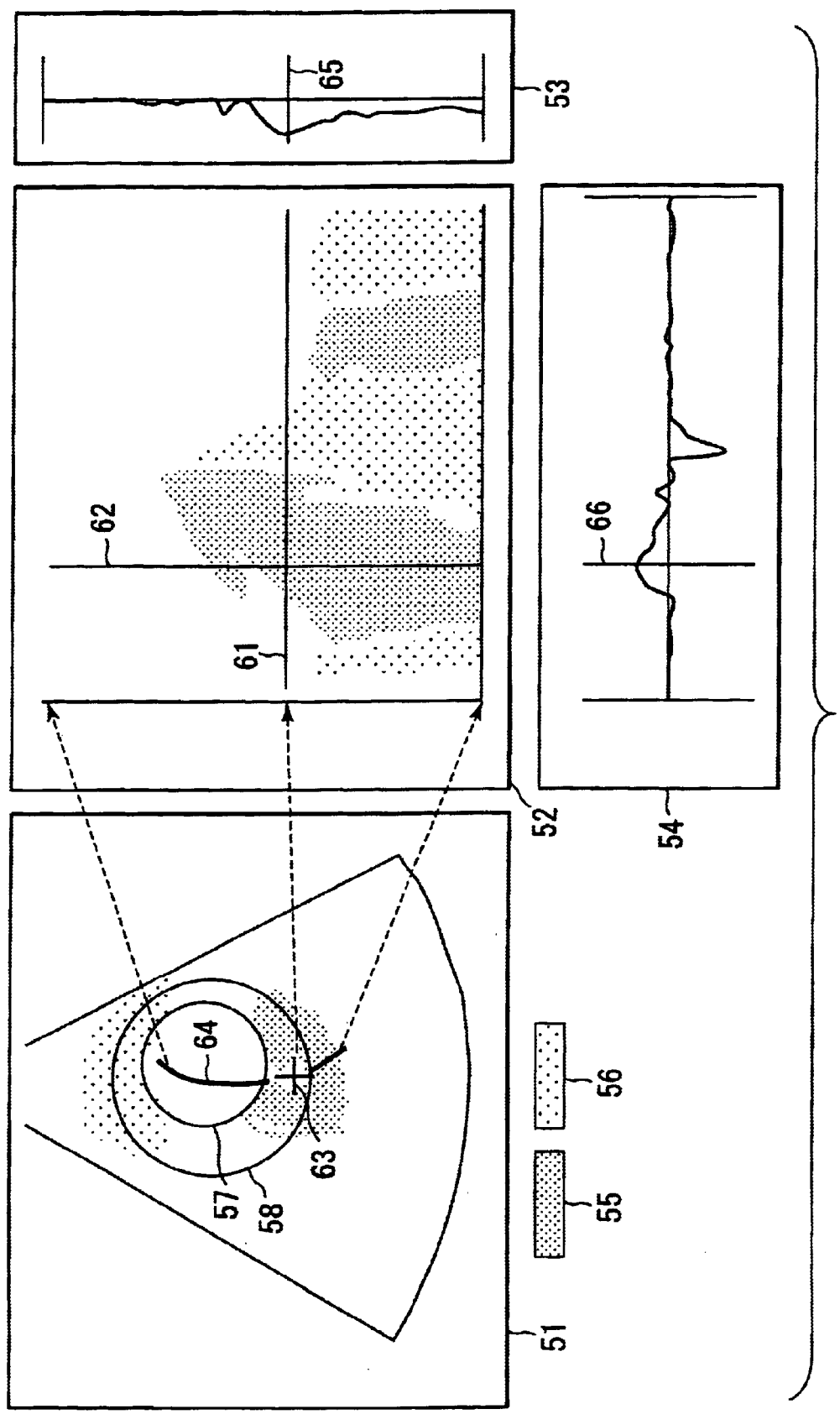
FIGS. 6A and 6B are views showing actual examples of an arbitrary M-mode image and cross-profile which are obtained by the first embodiment of the present invention.
Figure 6B:
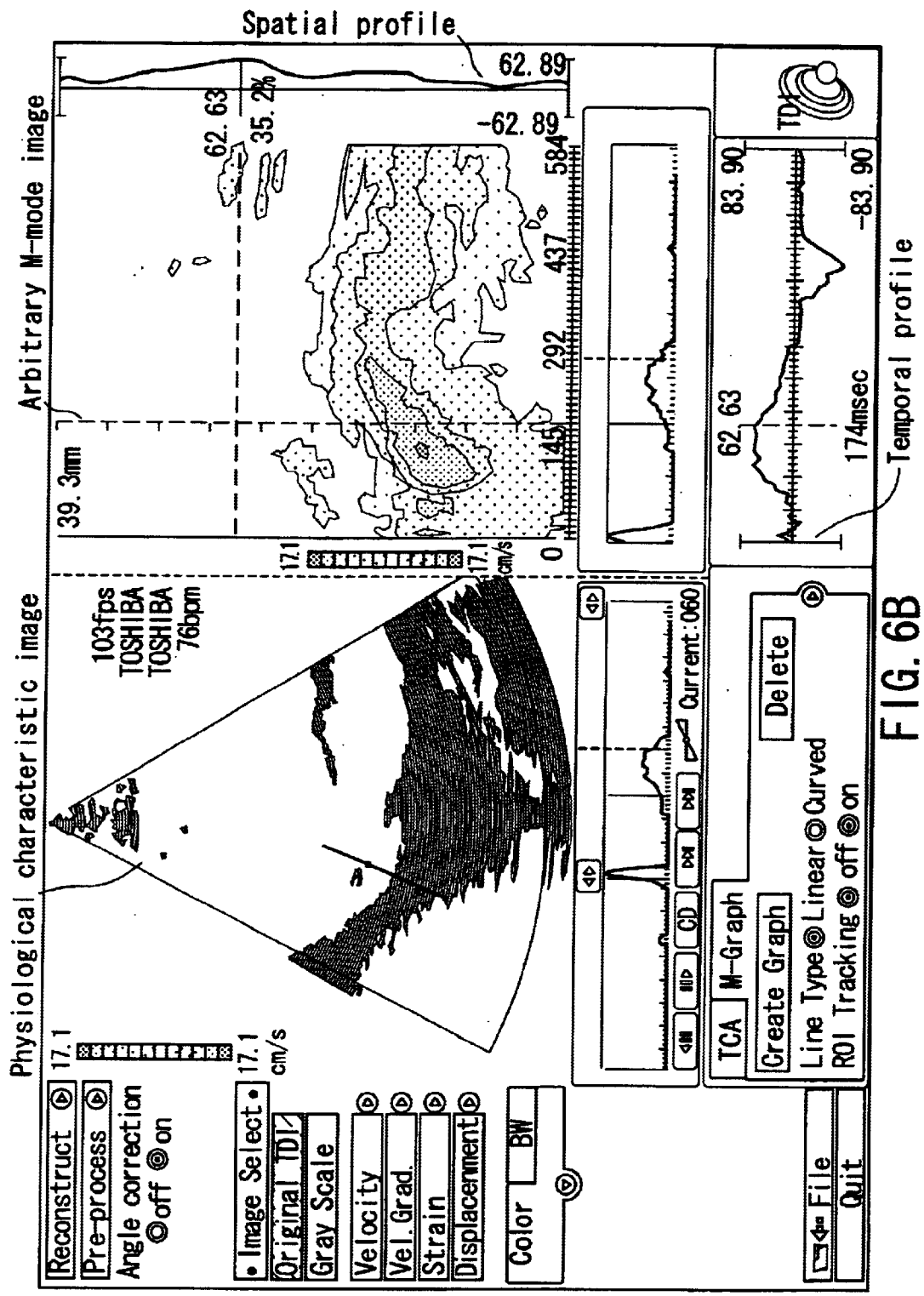

FIG. 6A shows actual examples of an arbitrary M-mode image obtained in the first embodiment and cross-profile. A two-dimensional image displayed in the first image display area 51 is a short axis image of the heart. The motion velocity of the cardiac muscle surrounded by boundary lines 57 and 58 is displayed in a pattern 55 when the cardiac muscle approaches the ultrasound probe 1, and is displayed in a pattern 56 when the cardiac muscle separates from the ultrasound probe 1. An arbitrary M-mode image, spatial profile, and temporal profile are respectively displayed in the second image display area 52, first profile display area 53, and second profile display area 54 when the LOI 64 and orthogonal position marker 63 are set on the posterior wall of the cardiac muscle on this two-dimensional image. The coordinates of the space marker 65, the time phase of the time marker 66, the numeric values of physiological characteristics, and the like are displayed on the respective profiles. FIG. 6B shows an example of the display form of the coordinates of the space marker 65, the time phase of the time marker 66, and the like.

The first modification of this embodiment will be described next with reference to FIGS. 7 and 8.

The first embodiment described the case wherein one LOI 64 is set on a two-dimensional image. In contrast to this, the first modification will describe a case wherein LOIs 64 are set at a plurality of positions, and a plurality of arbitrary M-mode images are displayed on the basis of physiological characteristics obtained from the LOIs 64. Clinically, in many cases, a plurality of LOIs 64 are set to compare a normal region with an abnormal region. A case wherein two LOIs are set will therefore be described below.

The operator operates the input section 9 to select the number of LOIs, a display scheme for the arbitrary M-mode (the display method shown in FIG. 7 or 8), and the like. The operator further sets two LOIs 64-1 and 64-2 on the two-dimensional image displayed in the first image display area 51. Assume that the physiological characteristics obtained from the two LOIs 64-1 and 64-2 are to be displayed as an arbitrary M-mode image and cross-profiles. In this case, according to the display method in FIG. 7, display areas 52-1 and 52-2 for arbitrary M-mode images and spatial profile display areas 53-1 and 53-2 and temporal profile display areas 54-1 and 54-2 for cross-profiles are independently provided for the respective LOIs, and are arranged on upper and lower layers, respectively.

In this case, arbitrary M-mode images, temporal profiles, and spatial profiles are to be displayed together as one set. This method is suited to a case wherein images are enlarged/displayed on a set basis by using floating windows.

In this case, time bars 62-1 and 62-2 on arbitrary M-mode images on the upper and lower layers preferably move in synchronism with each other (as one time bar 62 is moved, the other time bar automatically follows the movement) in consideration of the correspondence with the time phases of two-dimensional images. In contrast, the vertical movements of horizontal bars 61-1 and 61-2 and space markers 65-1 and 65-2 designed to follow their movements can be independently controlled.

In this case, in order to facilitate association between the two LOIs 64-1 and 64-2, arbitrary M-mode images, and accompanying cross-profiles, for example, the word "up" is added to each of the arbitrary M-mode image and cross-profiles displayed on the upper layer and the corresponding first LOI 64-1 when they are displayed. Likewise, the word "down" is added to each of the arbitrary M-mode image and cross-profiles displayed on the lower layer and the corresponding second LOI 64-2 when they are displayed. Note that this identification method is not limited to the above method. For example, line segments indicating the two LOIs 64-1 and 64-2 and the outer frames of M-mode images and cross-files are made to correspond in color to each other to be identified.

Figure 8:
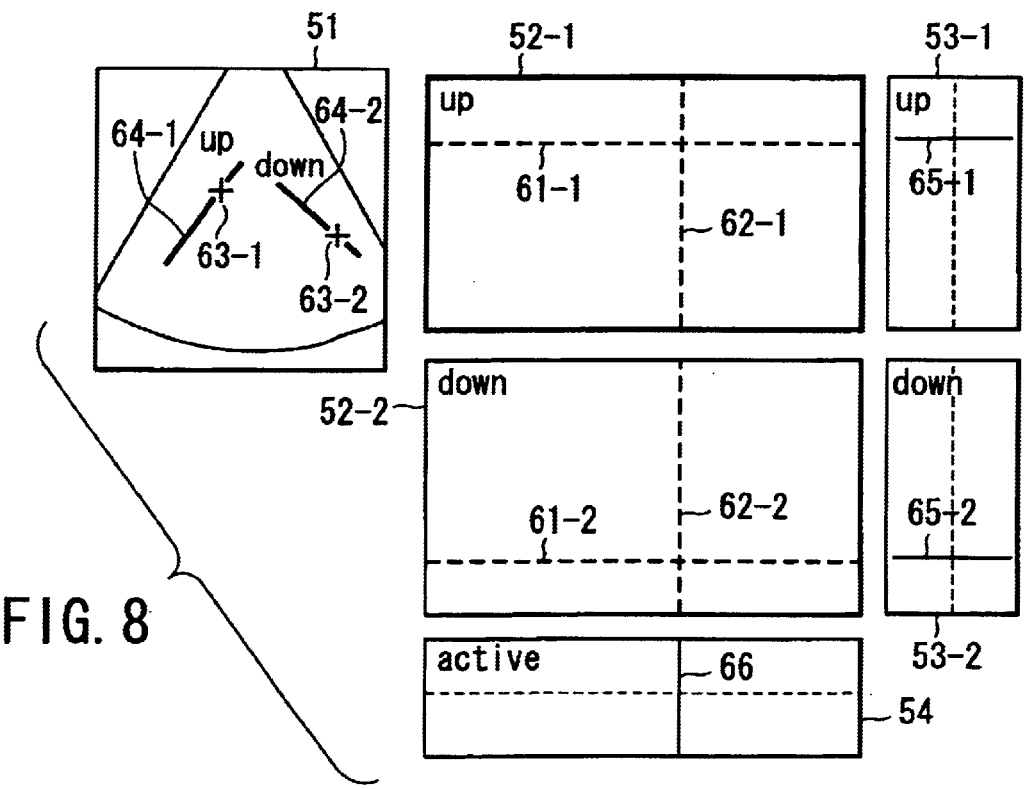
FIG. 8 is a view showing a modification of the first embodiment of the present invention.

In the display method in FIG. 8, only one second profile display area 54 is provided, and a selected one of a temporal file corresponding to the first LOI 64-1 and a temporal file corresponding to the second LOI 64-2 is displayed in the second profile display area 54. According to this display method, since arbitrary M-mode images and cross-files can be further enlarged and displayed, observation thereof is facilitated.

In this case, however, the temporal profile displayed in the second profile display area 54 must be identified to clearly show which one of the LOIs is displayed. When, for example, a temporal file corresponding to the first LOI 64-1 is displayed as shown in FIG. 8, the arbitrary M-mode image on the upper layer is surrounded by a thick box to indicate that the temporal file corresponding to the position of the horizontal bar 61 on this image is displayed in the second profile display area 54.

Figure 7:
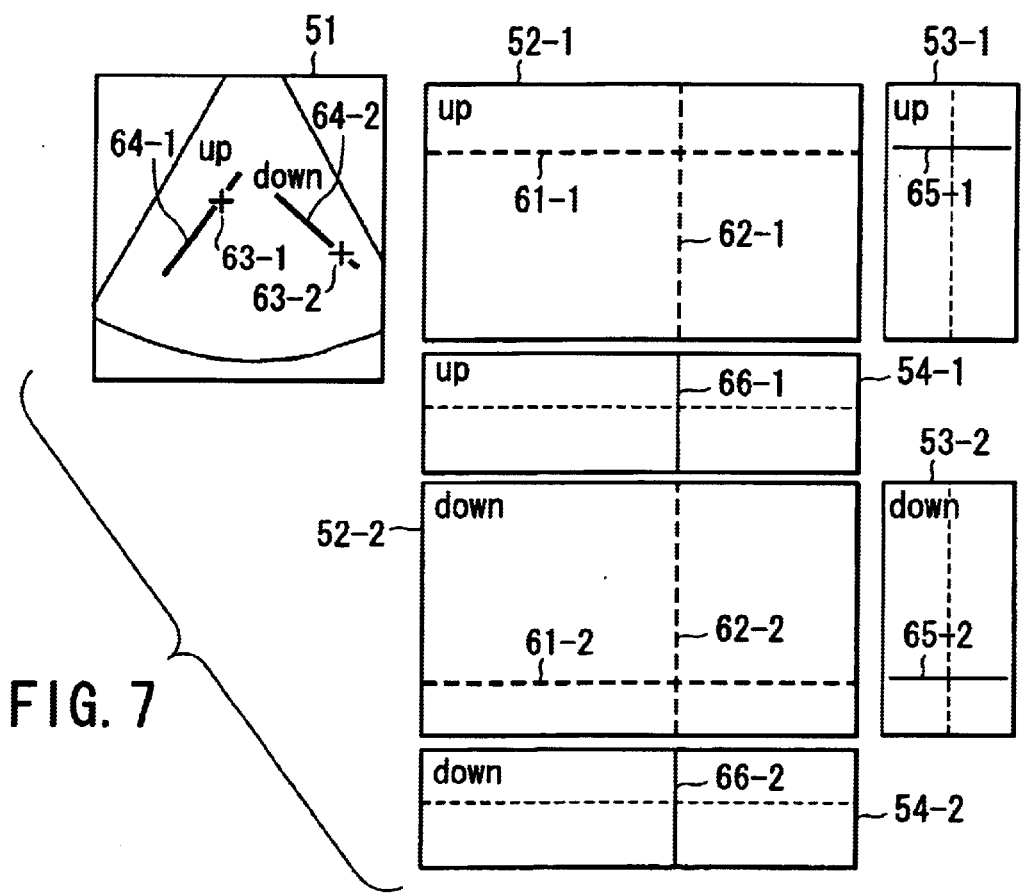
FIG. 7 is a view showing a modification of the first embodiment of the present invention.

As in the case shown in FIG. 7, in this display method as well, the movement of the time bar 62-1 on the arbitrary M-mode image on the upper layer is synchronized with the time bar 62-2 on the arbitrary M-mode image on the lower layer, and the horizontal bars 61-1 and 62-2 can be independently moved.

An application of the present invention to the ROI tracking method will be described next as the second modification of this embodiment. In this case, the "ROI tracking method" is a method of tracking ROIs in a time-series manner when the position and length of an LOI 64 are changed in accordance with temporal variations in the local position and size of the cardiac muscle in displaying arbitrary M-mode images associated with the cardiac muscle. Since this method is disclosed in Jpn. Pat. Appln. KOKAI Publication Nos. 10-151133 and 10-71147, a detailed description thereof will be omitted.

That is, this embodiment employs an LOI tracking method of tracking an LOI by using the above ROI tracking method. Assume that such an LOI 64 is tracked, and arbitrary M-mode display is performed by the same method as described in the first embodiment. In this case, since the length of the LOI 64 can change over time, display is performed with an undefined spatial length (the width of an M-mode display in the longitudinal direction).

In order to solve this problem, the length of the LOI 64 in each time phase is standardized and assigned to a display length. This makes it possible to regard a spatial direction as a relative position, and hence allows cross-profile to be applied to an arbitrary M-mode image accompanied by ROI tracking. In this case, however, a temporal profile indicates temporal changes in physiological characteristic at the relative position of the LOI 64, and a spatial profile indicates spatial changes in physiological characteristic at the relative position of the LOI 64. Note that [%] display of spatial position information described in the first embodiment is suited to such relative position display.

Cross-profile in the first embodiment described above is used to make an analysis matched with the display coordinate system of an arbitrary M-mode image. In a temporal profile, in particular, a physiological characteristic at a position corresponding to the linear horizontal bar 61 is displayed. Such a profile allows the operator to quantitatively evaluate a physiological characteristic by moving the cross cursor 60 to a desired position on an obtained arbitrary M-mode image, and hence becomes a very useful tool for the purpose of understanding an arbitrary M-mode image in detail. For example, observing the spatial profile of a tissue velocity with the LOI 64 being set in the transmural direction of the cardiac muscle allows the operator to grasp an intramyocardial velocity distribution. This makes it possible to provide clinically useful information as well.

(Second Embodiment)

In some cases, however, more useful diagnosis information can be provided by tracking the movement of the same local tissue in a temporal profile with an LOI 64 being set in the transmural direction of the cardiac muscle. This embodiment will describe the temporal profile of a physiological characteristic obtained at an analysis position which is set on the tracked line obtained by tracking the movement of a specific local tissue instead of lineally setting an acquisition position for the temporal profile of an arbitrary M-mode image. Note that the operator may manually set a tracked line by moving the mouse cursor on the display window. This method, however, takes a lot of trouble, and imposes a heavy load on the operator. For this reason, it is preferable to use the method of obtaining a tracked line by automatically tracking the movement of tissue.

As a conventional automatic tracking means for M-mode images, a so-called TDT (tissue-Doppler-tracking) method is disclosed in Jpn. Pat. Appln. KOKAI Publication No. 9-201361, which can track the locus of the movement of a specific region of tissue more accurately from the positional information of the tissue obtained by M-mode scanning and the movement velocity information of the region, as has already been described above.

The second embodiment in which cross-profile is performed by applying this TDT method to the arbitrary M-mode method will be described below with reference to FIGS. 9A to 11. In order to make the TDT method effectively function in arbitrary M-mode display, the direction in which the linear LOI 64 is set needs to coincide with the moving direction of a specific region on the LOI 64, and a velocity component in the moving direction needs to be able to be measured by the tissue Doppler method.

Figure 9A:
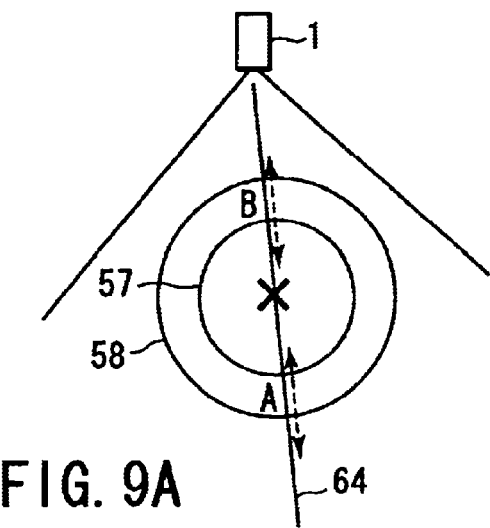
FIGS. 9A and 9B are views showing the relationship between an LOI and a tissue motion direction in the second embodiment of the present invention.
Figure 9B:
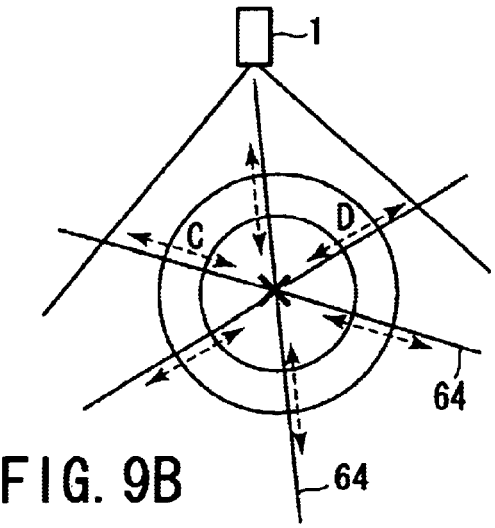

As is generally known, when the movement velocity of tissue is to be obtained by the tissue Doppler method, a movement velocity component parallel to the beam direction of ultrasound waves is measured. FIG. 9A shows a case wherein the conventional M-mode method is applied to the systolic and diastolic motions of the heart in its short axis image. In this case, the LOI 64 in the conventional M-mode method is set to extend from the ultrasound probe 1 as a starting point in the ultrasound transmission/reception direction with respect to the heart which repeats systolic and diastolic motions in the directions indicated by the arrows with "X" in the heart chamber being the center. For this reason, the above conditions are satisfied in only areas A and B. That is, the application range of the TDT method is very narrow. In contrast to this, according to the arbitrary M-mode method, as shown in FIG. 9B, if the LOI 64 is so set as to pass through a systolic center X of a short axis image of the heart, the TDT method can be effectively applied to the systolic and diastolic motions of the cardiac muscle. In this case as well, movement velocity components in the systolic center direction need to be obtained by the tissue Doppler method. It is difficult to detect velocity components in the systolic and diastolic directions in an area where the Doppler angle (the angle defined by a motion direction and an ultrasound beam direction) is 90°. However, the application region greatly expands compared with the conventional M-mode method in FIG. 9A.

Figure 10:
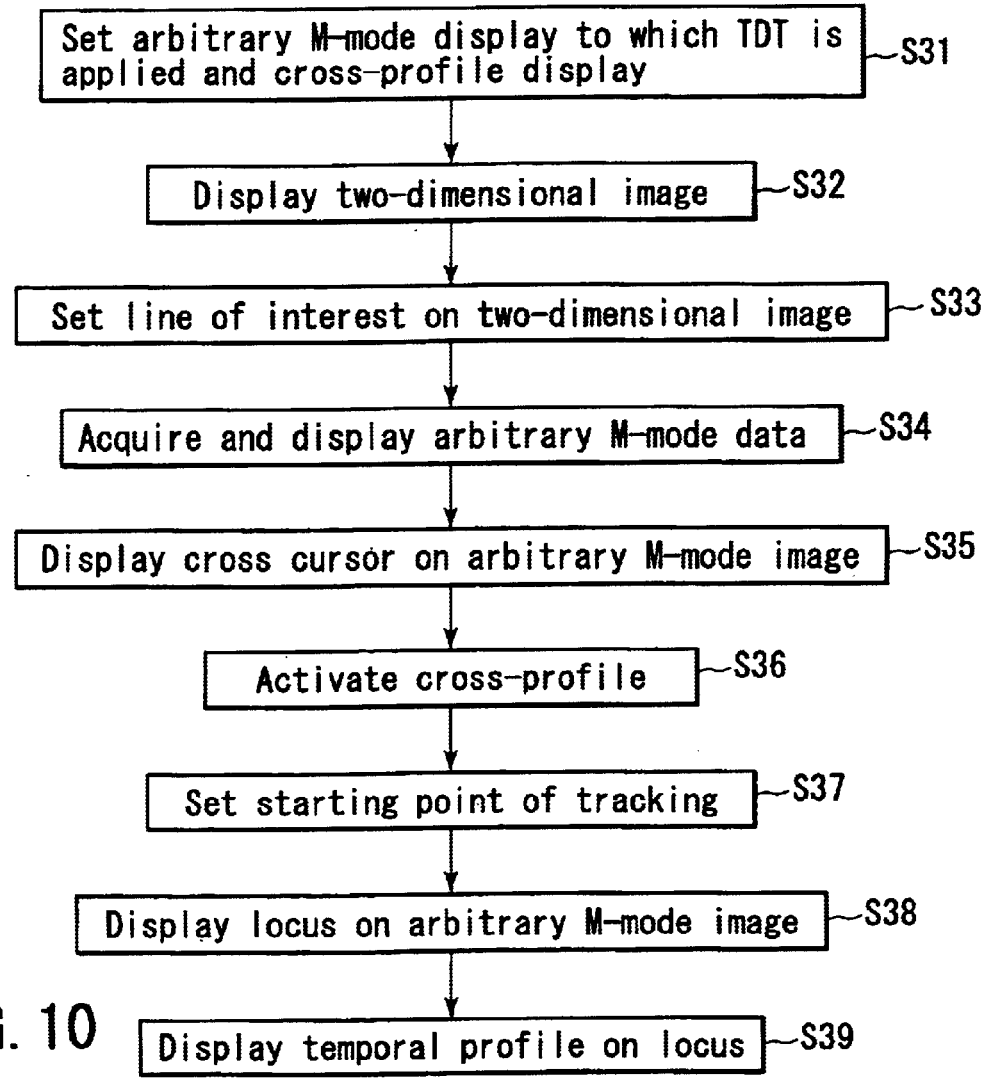
FIG. 10 is a flow chart showing a sequence for displaying an arbitrary M-mode image and temporal profile in the second embodiment of the present invention.

A sequence for displaying an arbitrary M-mode image and temporal profile in the second embodiment will be described next with reference to the flow chart of FIG. 10.

When the operator presses selection buttons for arbitrary M-mode display and cross-profile display to which the TDT method is applied, the corresponding command signals are sent to an image processor 29 through a system control section 8. The image processor 29 displays a display window like the one shown in FIG. 4 on a display section 10 (step S31).

First of all, the operator selects proper two-dimensional image data from the image data stored in an image storage circuit 28 and displays it in a first image display area 51. In general, however, when the operator inputs an arbitrary M-mode command signal to the image processor 29 with the input section 9, two-dimensional image data acquired first (i.e., image data in the time phase t1) is automatically displayed in the first image display area 51 (step S32).

The operator moves an orthogonal position marker 63 displayed on the two-dimensional image (a) displayed in the first image display area 51 in FIG. 4 by using the mouse of the input section 9 to set the linear LOI 64 at an arbitrary position on the two-dimensional image. The image processor 29 measures the total length of this LOI 64 and divides the total length into predetermined lengths, thereby determining a position where arbitrary M-mode information (tissue movement velocity) (step S33).

When the LOI 64 is set by the operator, the image processor 29 reads the coordinates of each point on the LOI 64. The image processor 29 then reads out the movement velocities of the tissue at the respective positions from the M tissue Doppler image data stored in the image storage circuit 28, and sequentially displays them in a second image display area 52 in time series. Assume that, in the image data acquisition in step SB, M two-dimensional image data corresponding to one heartbeat are to be acquired and stored in the image storage circuit 28. In this case, the image processor 29 reads out velocity information at a predetermined position on the LOI 64 which has already been set in each two-dimensional image data, and sequentially displays the information in the time axis direction of the second image display area 52 in the order of image data acquisition, thereby generating an arbitrary M-mode image corresponding to one heartbeat (step S34).

When the operator clicks an arbitrary position on the arbitrary M-mode image displayed in the second image display area 52 by using the mouse, a cross cursor (cross line) 60 is displayed at the clicked position (step S35). At the same time, a cross-profile is activated (step S36). The operator can set the central position of the cross cursor 60, a horizontal bar 61 (which is the horizontal line of the cross cursor 60), and a time bar 62 (which is the vertical line of the cross cursor 60). The operator clicks the central position of the cross cursor 60 by using the mouse, and drags it in an arbitrary direction or independently drags the horizontal bar 61 in the vertical direction, and the time bar 62 in the horizontal direction, thereby moving the central position to a desired position.

The operator moves the central position of the cross cursor 60 by using the mouse to set a time phase as the starting point of tracking and a region of a tissue (step S37). The image processor 29 reads out the set two-dimensional image from the image storage circuit 28 and displays it in the first image display area 51. In addition, the image processor 29 displays the position of the starting point set on the LOI 64 displayed on this image by using the orthogonal position marker 63.

When the position of the starting point is set on the two-dimensional image, the operator inputs a track command through the input section 9. Upon reception of this command, the image processor 29 reads out the coordinates of the position of the starting point and the value of the movement velocity from the image data in the image storage circuit 28. The image processor 29 estimates the coordinates of the first movement point after a unit time (corresponding to one time phase) on the basis of these data and displays the estimated coordinates as a tracking line on the M-mode image. The image processor 29 then selects a two-dimensional image in the next time phase, and reads out the value of a tissue velocity at the first movement point on this image from this image data. The image processor 29 further estimates the coordinates of the second movement point in the next time phase from this movement point and the tissue velocity thereat, and displays the estimated coordinates on the M-mode image.

When the image processor 29 repeats this operation, the locus of the motion of the initially set starting point is displayed upon being superimposed on the arbitrary M-mode image (step S38). In addition, the movement velocity of the tissue on this tracking line is displayed as a temporal file in a second profile display area 54 (step S39).

Figure 11:
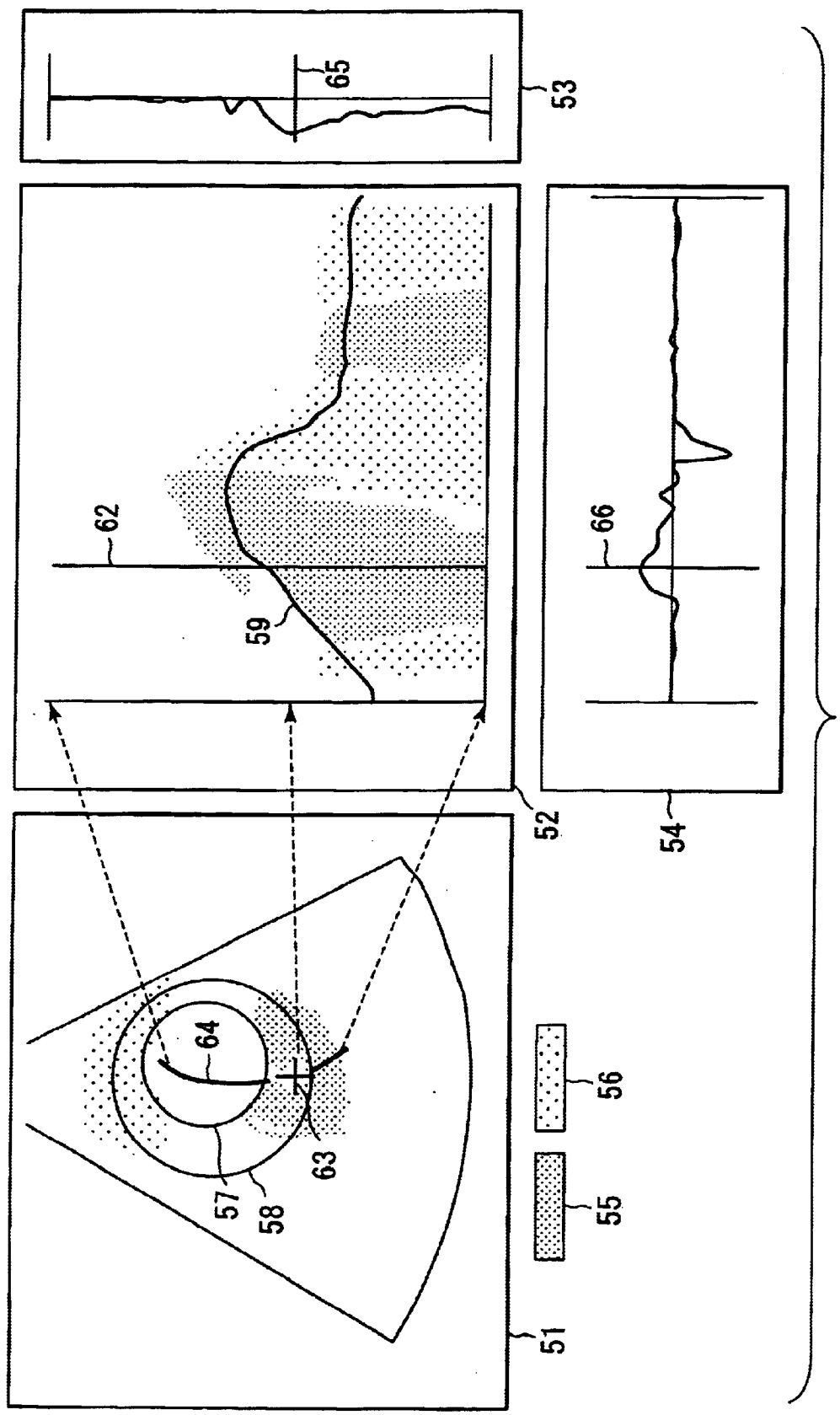
FIG. 11 is a view showing an arbitrary M-mode image and temporal profile which are obtained by the second embodiment of the present invention.

FIG. 11 shows an arbitrary M-mode image and temporal profile obtained in this embodiment. The tracking line of a motion in the region designated by the orthogonal position marker 63 on the two-dimensional image is displayed as a line 59. The display in FIG. 11 differs from that in FIG. 6 in that the horizontal bar 61 becomes a tracking line (line 59), and the position of the marker 63 becomes a point corresponding to the intersection of the time bar 62 and the tracking line. Other display methods are the same as those shown in FIGS. 6A and 6B, and hence a description thereof will be omitted. In this embodiment, importance is attached to observation of temporal changes, and a spatial profile 53 is not necessarily important. Therefore, a display method without any spatial profile may be used.

As described above, according to the second embodiment, since the movement of a specific region in a case wherein the LOI 64 is set in the transmural direction of the cardiac muscle can be tracked, the temporal profile of a physiological characteristic in the same region can be easily obtained. Therefore, this makes it possible to accurately quantify a physiological characteristic in a specific region.

When a velocity is to be obtained by the tissue Doppler method, a velocity value tends to be spatially unstable due to the influences of speckle noise and the like unique to ultrasound waves. For this reason, display of an arbitrary M-mode image having a velocity as a physiological characteristic also tends to be spatially unstable, resulting in a deterioration in the velocity precision of a cross-profile.

It is known that since this speckle noise spatially varies and is distributed, a stable velocity value can be obtained by averaging velocities obtained in a plurality of spaces separated from each other at small intervals. When the velocity value of a specific region is to be estimated from an arbitrary M-mode image, there is a tradeoff with spatial resolution.

Effective spatial averaging may be realized by not only displaying the value of a physiological characteristic on the LOI 64 without any change as shown in FIG. 12A but also making correction by using physiological characteristics near the LOI 64. More specifically, when an arbitrary M-mode image is to be formed, the image processor 29 selects a plurality of areas (three areas in FIG. 12B) in the direction of the normal to the LOI 64 set as shown in FIG. 12B. The image processor 29 then estimates the tissue velocity at the LOI 64 from the weighted average of physiological characteristics (velocity values in this case) in the plurality of areas, and displays the resultant data as M-more image data in the second image display area 52.

In the spatial direction of the LOI 64 (the line direction of the LOI 64), no averaging processing or weak averaging processing is performed. According to this method, a stable arbitrary M-mode image can be obtained while the resolution in the spatial direction is maintained. Therefore, an accurate tissue velocity value can be stably obtained in cross-profile as well, and the reliability of an analysis result improves.

More specifically, when an arbitrary M-mode image is to be generated, an intramyocardial velocity distribution can be stably evaluated by setting the linear LOI 64 in the transmural direction of the cardiac muscle and performing averaging processing in a wall direction perpendicular to the transmural direction. Note that such averaging processing is effective in improving the stability of measurement when a physiological characteristics obtained by a velocity (e.g., a displacement or strain) or a physiological characteristic other than velocity (e.g., the luminance of a B-mode image) is to be analyzed.

Obviously, various modifications can be made from the arrangement of the present invention within the spirit and scope of the invention in addition to the above embodiments and their modifications.

For example, referring to FIG. 4, as is obvious, the space marker 65 and time marker 66 are effective in associating the first profile display area 53, second profile display area 54, and second image display area 52. Even in the presence of offsets or with different sizes, M-mode display and orthogonal profiles can be easily associated with each other by making the time marker 66, time bar 62, and space marker 65 correspond to each other.

In addition, the orthogonal position marker 63 may have any shape as long as the position of the horizontal bar 61 of the cross cursor 60 can be displayed with respect to the LOI 64 set in a two-dimensional image.

Various modifications can be applied to the arrangement of the respective display areas within the spirit and scope of the present invention. For example, as shown in FIG. 13, the temporal profile display area may be placed above the M-mode image display area, and the spatial profile display area 53 may be placed on the left side of the M-mode image display area.

Figure 14:
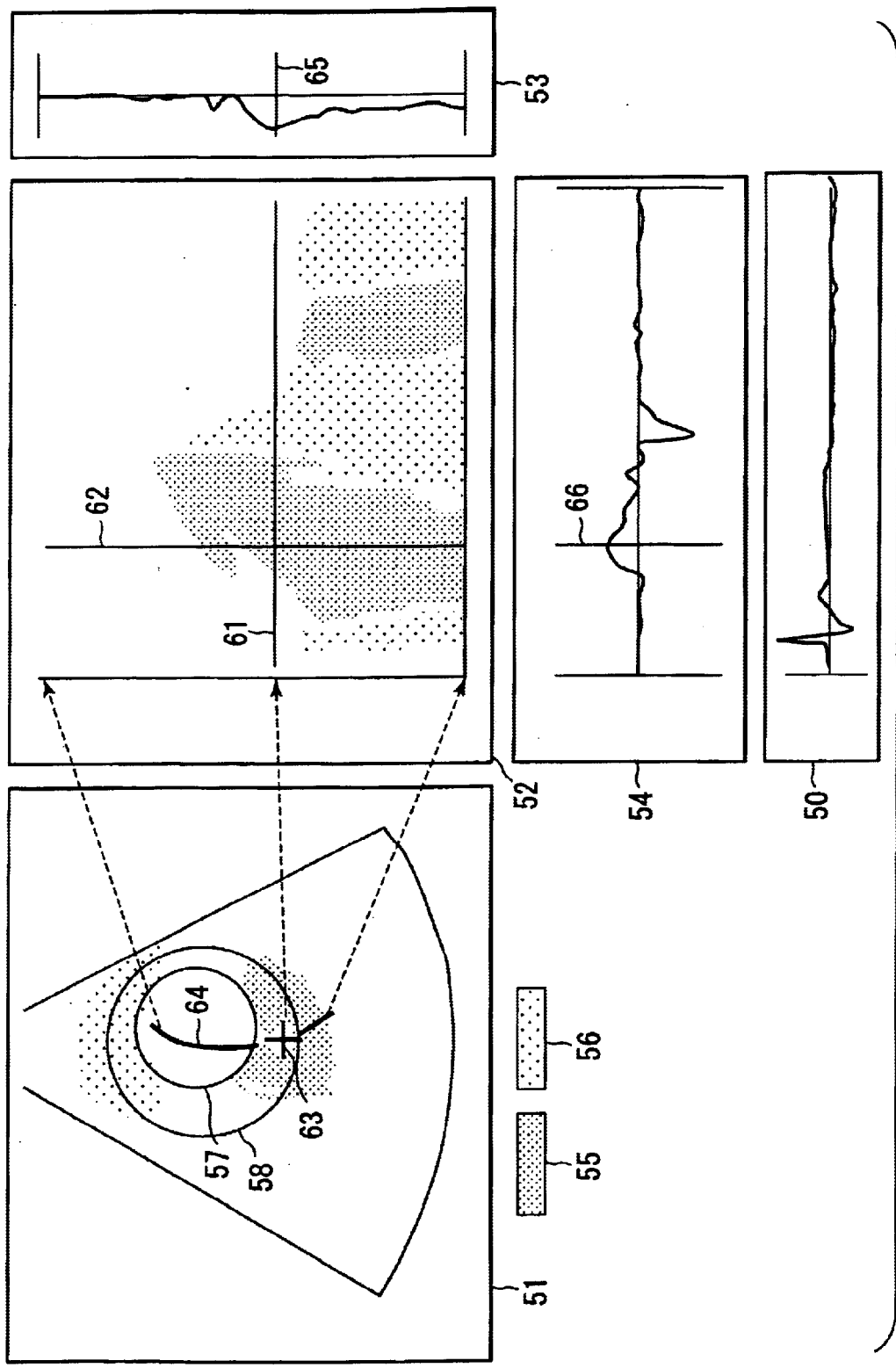
FIG. 14 is a view showing a method of displaying images including an ECG waveform in the first and second embodiments of the present invention.

In addition, when the heart is to be diagnosed, it is important to evaluate a temporal profile together with a biometric signal (e.g., an ECG waveform (electrocardiographic waveform)). FIG. 14 shows a case wherein an ECG waveform is displayed in a biometric signal display area 50 in correspondence with a temporal profile. In this display example of the ECG waveform as well, standardization is performed with the maximum absolute value of the amplitude, and the maximum value is displayed.

When an ultrasound image displayed in the first display area shown in, for example, FIG. 4 contains a plurality of physiological characteristics, the temporal and spatial profiles of each of two of the physiological characteristics may be simultaneously displayed (double cross-file display). More specifically, assume that an ultrasound image contains two physiological characteristics, i.e., the intensity (luminance) of a B-mode image and the tissue velocity of a tissue Doppler image. In this case, an arbitrary M-mode image associated with luminance or tissue velocity may be generated. In addition, temporal profiles associated with the luminance and tissue velocity and spatial profiles associated with the luminance and tissue velocity may be simultaneously displayed above and below the arbitrary M-mode image and on the left and right sides of the arbitrary M-mode image, respectively. In this double cross-file display, it is more preferable that the profiles corresponding to the physiological characteristics indicated by the arbitrary M-mode image be so displayed as to be identifiable.

Each of the above embodiments has described the case wherein an arbitrary M-mode image is constituted by two-dimensional images. However, the present invention is not limited to this. For example, the techniques according to the present invention can also be applied to a case wherein the linear LOI 64 is set for a three-dimensional image data set, and an arbitrary M-mode image is displayed. An operation sequence in this case can be separated from the main body of the ultrasound diagnosis apparatus, and an arbitrary M-mode image and cross-profile can be displayed by a computer such as a PC or workstation.

Figure 15:
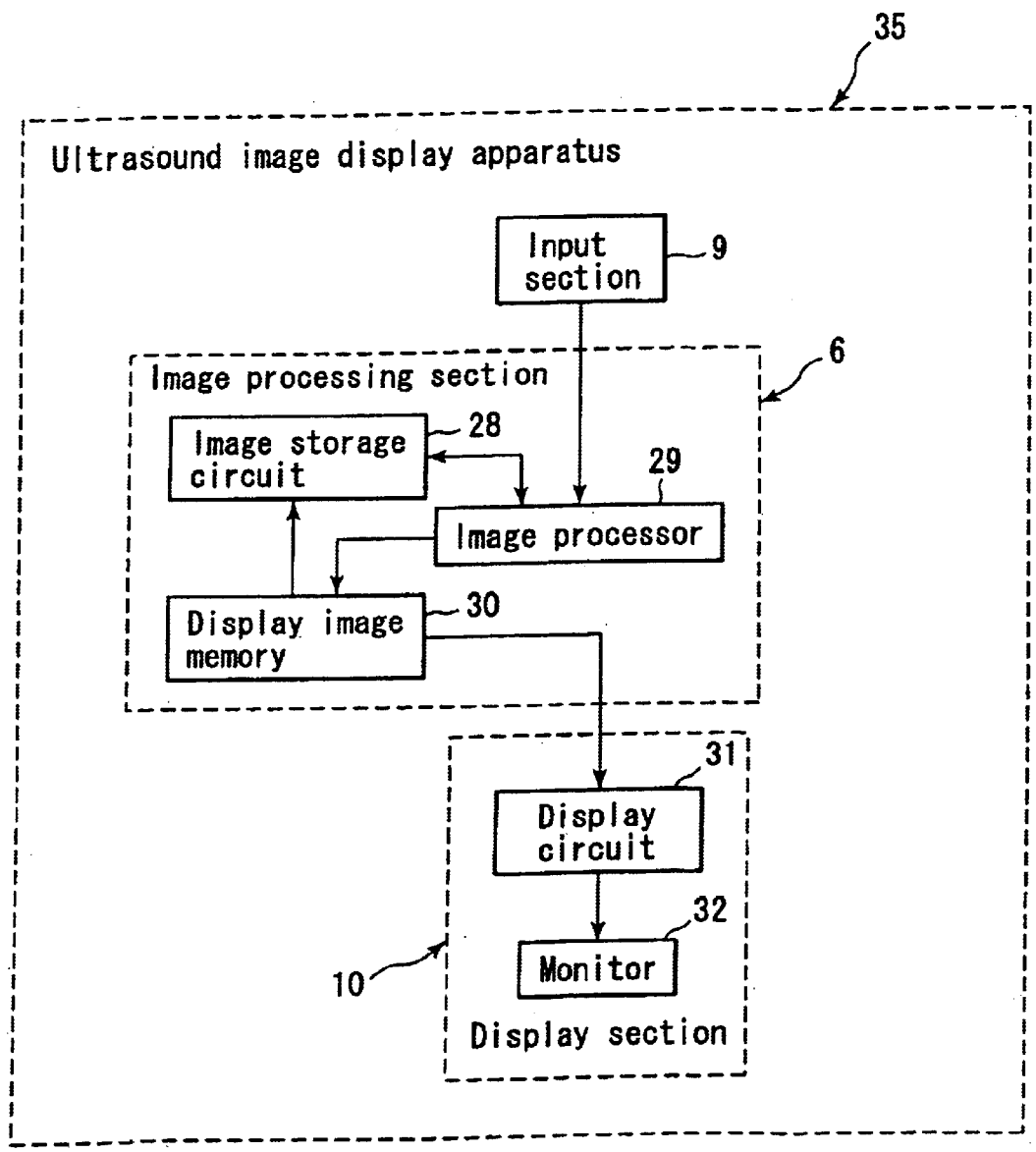
FIG. 15 is a block diagram showing the arrangement of an ultrasound image display apparatus according to the present invention.

The means for generating an arbitrary M-mode image and cross-profile in the present invention can be formed separately from the two-dimensional generating means formed by the ultrasound diagnosis apparatus. More specifically, the above means can be independently formed as an ultrasound image display apparatus 35 including an input section 9, image processing section 6, and display section 10, as shown in FIG. 15. In this case, a plurality of ultrasound image data to be stored in an image storage circuit 2B of the image processing section 6 are supplied from a separately formed ultrasound diagnosis apparatus through a storage medium or communication cable. Note that since a cross-file display sequence in this ultrasound image display apparatus is the same as the flow charts of FIGS. 3 and 10, a description thereof will be omitted.

In addition, the function of the above ultrasound diagnosis apparatus can be implemented as software. That is, each function described in each embodiment can be executed as a program for causing a computer to execute a predetermined function. In addition, each function can also be implemented by installing the program into a computer from a computer-readable recording medium on which the program is recorded.

As described above, according to this embodiment, motion information of a living tissue in an arbitrary region in the living body, blood flow dynamics information, and the like can be easily quantified. In addition, the quantified position of tissue can be easily checked on a two-dimensional image. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnosis apparatus comprising:

an ultrasound probe which includes ultrasound transducers which transmit and receive ultrasound waves to and from an object to be examined;

an ultrasound transmission/reception unit which transmits and receives an ultrasound beam by driving the ultrasound transducers;

a physiological characteristic image data generating unit which generates physiological characteristic image data corresponding to at least one time phase, which is used to image at least one physiological characteristic of the object, on the basis of a reception signal received by the ultrasound transmission/reception unit;

a memory which stores the physiological characteristic image data;

an LOI (Line Of Interest) setting unit which sets an LOI at an arbitrary position on a physiological characteristic image displayed on the basis of the physiological characteristic image data;

an M-mode image generating unit which reads out the physiological characteristic image data corresponding to the LOI from the memory and generates an arbitrary M-mode image as an M-mode image representing a temporal change associated with the LOI;

a setting unit which sets a profile position by using a cursor displayed on the arbitrary M-mode image;

a profile generating unit which generates a temporal profile of the arbitrary M-mode image at the profile position and a spatial profile of the arbitrary M-mode image which is associated with a line segment including at least the LOI; and a display unit which simultaneously displays the arbitrary M-mode image, the temporal profile, and the spatial profile.

2. An apparatus according to claim 1, wherein the cursor comprises a cross cursor which is constituted by a first straight line and a second straight line crossing the first straight line at a right angle, with the respective straight lines and an intersection point thereof moving on the arbitrary M-mode image in accordance with an instruction from an operator, and the profile generating unit generates the temporal profile corresponding to a position of the first straight line, and generates the spatial profile corresponding to a position of the second straight line.

3. An apparatus according to claim 1, wherein the display unit places the temporal profile on the lower or upper side of the arbitrary M-mode image, and places the spatial profile on the right or left side of the arbitrary M-mode image.

4. An apparatus according to claim 1, wherein the display unit displays the ultrasound image, on which at least one of an LOI set on the physiological characteristic image and the profile position is identified, simultaneously with the arbitrary M-mode image, the temporal profile, and the spatial profile.

5. An apparatus according to claim 4, wherein the display unit displays a time phase of the ultrasound image and a time phase of the temporal profile in correspondence with each other.

6. An apparatus according to claim 4, wherein when a length of an LOI set on the ultrasound image changes over time, the display unit performs display upon controlling at least a length of an M-mode display axis corresponding to the LOI length to be constant.

7. An apparatus according to claim 1, wherein the physiological characteristic includes one of a strain amount of tissue, a strain ratio of tissue, a movement amount of the tissue, a movement velocity of at least one of the tissue or blood, and a correlation amount of the reception signal power.

8. An apparatus according to claim 1, wherein when the physiological characteristic image data includes at least two physiological characteristics, the M-mode image generating unit generates the arbitrary M-mode image associated with a designated one of the physiological characteristics.

9. An ultrasound diagnosis apparatus comprising:

an ultrasound probe which includes ultrasound transducers which transmit and receive ultrasound waves to and from an object to be examined;

an ultrasound transmission/reception unit which transmits and receives an ultrasound beam by driving the ultrasound transducers;

a physiological characteristic image data generating unit which generates physiological characteristic image data corresponding to a plurality of time phases, which are used to image a physiological characteristic associated with a body of the object, on the basis of a reception signal received by the ultrasound transmission/reception unit;

a memory which stores the physiological characteristic image data;

an LOI setting unit which sets an LOI at an arbitrary position on a physiological characteristic image displayed on the basis of the physiological characteristic image data;

an M-mode image generating unit which reads out the physiological characteristic image data corresponding to the LOI from the memory and generates an arbitrary M-mode image which is an M-mode image indicating a temporal change associated with the LOI;

a setting unit which sets a specific region whose motion is to be tracked in a time-series manner and a start time phase of tracking;

a specific region tracking unit which tracks a time-series position of the specific region from the start time phase by using the physiological characteristic image data corresponding to said plurality of time phases and acquires a tracking line associated with the specific region;

a profile generating unit which generates a temporal profile of the arbitrary M-mode image associated with the tracking line; and a display unit which simultaneously displays the arbitrary M-mode image and the temporal profile.

10. An apparatus according to claim 9, wherein the physiological characteristic image data comprises at least a movement velocity of tissue.

11. An apparatus according to claim 10, wherein the specific region tracking unit performs an angle correction for the movement velocity of the tissue in consideration of a direction of the LOI and the ultrasound transmission/reception direction, and obtains a tracking line for a specific region on the basis of a velocity component in the corrected predetermined motion direction.

12. An apparatus according to claim 9, wherein the display unit displays the tracking line on the arbitrary M-mode image.

13. An apparatus according to claim 9, wherein the display unit simultaneously displays the LOT and the ultrasound image for recognizing at least one of the specific regions, together with the arbitrary M-mode image and the temporal profile.

14. An apparatus according to claim 13, wherein the display unit displays a time phase of the ultrasound image and a time phase of the temporal profile in correspondence with each other.

15. An apparatus according to claim 9, wherein the profile generating unit further generates a spatial profile of the arbitrary M-mode image associated with a line segment containing at least the LOI, and the display unit simultaneously displays the arbitrary M-mode image, the temporal profile, and the spatial profile.

16. An apparatus according to claim 15, wherein the cursor moves on the arbitrary M-mode image displayed in accordance with an instruction from the operator, and comprises a first straight line and a second straight line crossing the first straight line at a right angle, and the profile generating unit generates the temporal profile corresponding to a position of the first straight line, and generates the spatial profile corresponding to a position of the second straight line.

17. An apparatus according to claim 15, wherein the display unit displays a marker at a position on the temporal profile which corresponds to the second straight line on the arbitrary M-mode image.

18. An apparatus according to claim 9, wherein the display unit displays the temporal profile on the lower or upper side of the arbitrary M-mode image.

19. An apparatus according to claim 9, wherein the display unit makes a display size of the temporal profile substantially coincide with a display size of the arbitrary M-mode image.

20. An apparatus according to claim 9, which further comprises a selection unit which selects at least one physiological characteristic of a strain amount of a tissue, a movement amount of the tissue, a movement velocity of the tissue, and a luminance, and in which the physiological characteristic includes one of a strain amount of tissue, a strain ratio of tissue, a movement amount of the tissue, a movement velocity of at least one of the tissue or blood, and a correlation amount of the reception signal power.

21. An apparatus according to claim 9, which further comprises a selection unit which selects one of physiological characteristics when the physiological characteristic image data includes at least two physiological characteristics, and
in which the M-mode image generating unit generates the arbitrary M-mode image associated with the selected physiological characteristic.

22. An apparatus according to claim 9, which further comprises a biometric signal measuring unit which measures a biometric signal waveform associated with the object, and
in which the display unit performs display upon making a display size of a time axis of the biometric signal waveform substantially coincide with a size of a time axis of the arbitrary M-mode image.

23. An apparatus according to claim 9, wherein the M-mode image generating unit calculates an average value of a plurality of physiological characteristics associated with an area adjacent to the LOI, and generates arbitrary M-mode image data of the specific region on the basis of the average value.

24. An ultrasound image display apparatus comprising:
a memory which stores physiological characteristic image data corresponding to at least one time phase, which is obtained by imaging at least one physiological characteristic of an object to be examined, on the basis of an ultrasound signal received from the object;
an LOI (Line Of Interest) setting unit which sets an LOI at an arbitrary position on a physiological characteristic image displayed on the basis of the physiological characteristic image data;
an M-mode image generating unit which reads out the physiological characteristic image data corresponding to the LOI from the memory, and generates an arbitrary M-mode image which is an M-mode image representing a temporal change associated with the LOI;
a setting unit which sets a profile position by a cursor displayed on the arbitrary M-mode image;
a profile generating unit which generates a temporal profile of the arbitrary M-mode image at the profile position and a spatial profile of the arbitrary M-mode image associated with a line segment containing at least the LOI; and
a display unit which simultaneously displays the arbitrary M-mode image, the temporal profile, and the spatial profile.

25. An ultrasound image display apparatus comprising:
a memory which stores physiological characteristic image data corresponding to at least one time phase, which is obtained by imaging at least one physiological characteristic of an object to be examined on the basis of an ultrasound signal received from the object;
an LOI (Line of Interest) setting unit which sets an LOI at an arbitrary position on a physiological characteristic image displayed on the basis of the physiological characteristic image data;
an M-mode image generating unit which reads out the physiological characteristic image data corresponding to the LOI from the memory, and generates an arbitrary M-mode image which is an M-mode image representing a temporal change associated with the LOI;
a setting unit which sets a specific region whose motion is to be tracked in a time-series manner and a start time phase of tracking by a cursor displayed on the arbitrary M-mode image;
a specific region tracking unit which tracks a time-series position of the specific region from the start time phase by using the physiological characteristic image data corresponding to said plurality of time phases and acquires a tracking line associated with the specific region;
a profile generating unit which generates a temporal profile of the arbitrary M-mode image associated with the tracking line; and
a display unit which simultaneously displays the arbitrary M-mode image and the temporal profile.

26. An ultrasound image display method comprising:
storing physiological characteristic image data corresponding to at least one time phase, which is obtained by imaging at least one physiological characteristic of an object to be examined on the basis of an ultrasound signal received from the object;
setting an LOI (Line Of Interest) at an arbitrary position on a physiological characteristic image displayed on the basis of the physiological characteristic image data;
reading out the physiological characteristic image data corresponding to the LOI from the memory, and generating an arbitrary M-mode image which is an M-mode image representing a temporal change associated with the LOI;
setting a profile position by a cursor displayed on the arbitrary M-mode image;
generating a temporal profile of the arbitrary M-mode image at the profile position and a spatial profile of the arbitrary M-mode image associated with a line segment containing at least the LOI; and
simultaneously displaying the arbitrary M-mode image, the temporal profile, and the spatial profile.

27. An ultrasound image display method comprising:
storing physiological characteristic image data corresponding to at least one time phase, which is obtained by imaging at least one physiological characteristic of an object to be examined on the basis of an ultrasound signal received from the object;
setting an LOI (Line Of Interest) at an arbitrary position on a physiological characteristic image displayed on the basis of the physiological characteristic image data;
reading out the physiological characteristic image data corresponding to the LOI from the memory, and generating an arbitrary M-mode image which is an M-mode image representing a temporal change associated with the LOI;
setting a specific region whose motion is to be tracked in a time-series manner and a start time phase of tracking by a cursor displayed on the arbitrary M-mode image;
tracking a time-series position of the specific region from the start time phase by using the physiological characteristic image data corresponding to said plurality of time phases and acquiring a tracking line associated with the specific region;
generating a temporal profile of the arbitrary M-mode image associated with the tracking line; and
simultaneously displaying the arbitrary M-mode image and the temporal profile.

28. An ultrasound image display apparatus comprising:

a memory which stores physiological characteristic image data corresponding to at least one time phase, which is obtained by imaging at least one physiological characteristic of an object to be examined on the basis of an ultrasound signal received from the object;

an LOI (Line Of Interest) setting unit which sets a plurality of LOIs at arbitrary different positions on a physiological characteristic image displayed on the basis of the physiological characteristic image data;

an M-mode image generating unit which reads out the physiological characteristic image data corresponding to the respective LOIs from the memory, and generates a plurality of arbitrary M-mode images which are M-mode images representing temporal changes associated with the respective LOIs;

a setting unit which sets a profile position for said each arbitrary mode image by cursors displayed on the respective arbitrary M-mode images;

a profile generating unit which generates, for said each arbitrary mode image, a temporal profile of the arbitrary M-mode image at the profile position and a spatial profile of the arbitrary M-mode image associated with a line segment containing at least the LOI; and a display unit which simultaneously displays the respective arbitrary M-mode images, the respective temporal profiles, and the respective spatial profiles.

29. An ultrasound image display apparatus comprising:

a memory which stores physiological characteristic image data corresponding to at least one time phase, which is obtained by imaging at least one physiological characteristic of an object to be examined on the basis of an ultrasound signal received from the object;

an LOI (Line Of Interest) setting unit which sets a plurality of LOIs at arbitrary different positions on a physiological characteristic image displayed on the basis of the physiological characteristic image data;

an M-mode image generating unit which reads out the physiological characteristic image data corresponding to the respective LOIs from the memory, and generates a plurality of arbitrary M-mode images which are M-mode images representing temporal changes associated with the respective LOIS;

a setting unit which sets, for said each arbitrary mode image, a specific region whose motion is to be tracked in a time-series manner and a start time phase of tracking by a cursor displayed on said each arbitrary M-mode image;

a specific region tracking unit which tracks a time-series position of the specific region from the start time phase by using the physiological characteristic image data corresponding to said plurality of time phases and acquires a tracking line associated with the specific region for said each arbitrary M-mode image;

a profile generating unit which generates a temporal profile of the arbitrary M-mode image associated with the tracking line for said each arbitrary M-mode image; and a display unit which simultaneously displays the respective arbitrary M-mode images and the respective temporal profiles.

* * * * *